(12) United States Patent
Takeda et al.

(10) Patent No.: US 7,022,893 B1
(45) Date of Patent: Apr. 4, 2006

(54) KNOCKIN GENE-MUTATED MOUSE COMPRISING A MUTANT PRESENILIN-1 GENE

(75) Inventors: Masatoshi Takeda, Osaka (JP); Junji Takeda, Osaka (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/581,528

(22) PCT Filed: Jan. 7, 1999

(86) PCT No.: PCT/JP99/00015

§ 371 (c)(1),
(2), (4) Date: Oct. 26, 2000

(87) PCT Pub. No.: WO99/34670

PCT Pub. Date: Jul. 15, 1999

(30) Foreign Application Priority Data

Jan. 8, 1998 (JP) .................................. 10-002191

(51) Int. Cl.
| A01K 67/00 | (2006.01) |
| A01K 67/027 | (2006.01) |
| C12N 15/00 | (2006.01) |
| C12N 5/00 | (2006.01) |

(52) U.S. Cl. .............................. 800/12; 800/3; 800/18; 800/25; 435/354

(58) Field of Classification Search .................... 800/3, 800/8, 9, 12, 13, 18, 25; 435/354
See application file for complete search history.

(56) References Cited

U.S. PATENT DOCUMENTS

| 5,650,550 A * | 7/1997 | Korach et al. .................. 800/2 |
| 5,877,399 A | 3/1999 | Hsiao et al. |
| 6,395,960 B1 * | 5/2002 | St. George-Hyslop et al. |
| 2002/0016978 A1 * | 2/2002 | Zheng et al. .................. 800/9 |
| 2002/0019992 A1 | 2/2002 | Hsiao et al. |

FOREIGN PATENT DOCUMENTS

| JP | 4-501501 | 3/1992 |
| WO | 89/09826 | 10/1989 |
| WO | 97/48792 | 12/1997 |

OTHER PUBLICATIONS

Wood PA. Phenotypic assessment: are you missing something? Comparative Medicine 50 (1): 12-15, 2000.*
Cameron ER. Recent advances in transgenic technology. Molecular Biotechnology 7:253-265, 1997.*
Hammer RE et al. Spontaneous inflammatory disease in transgenic rats expressing HLA-B27 and human beta2m: an animal model of HLA-b27 associated human disorders. Cell 63:1099-1112. 1990).*
Gardner RL and Brook FA. Reflections on the biology of embryonic stem (ES) cells. International J. of Dev. Biol. 41:235-243, 1997.*
Mullins LJ and Mullins.JJ. Transgenesis in the rat and larger mammals. J. Clin. Invest.97:1557-1560, 1996.*
Seamark, Progress and emerging problems in livestock transgenesis: a summary perspective. Reprod. Fertil. Dev. 6: 653-657, 1994.*
Guo et al. Nature Medicine 5:101-106, 1999.*
Tamaoka, A., Internal Medicine, vol. 77, 843-51 (1996).
Goate, A. et al., Nature, vol. 349, 704-6 (1991).
Murrell, J. et al., Science, vol. 254, 97-99 (1991).
Chartier-Harlin, M. et al., Nature, vol. 353, 844-46 (1991).
Mullan, M. et al., Nature Genetics, vol. 1, 345-47 (1992).
Hendricks, L. et al., Nature Genetics, vol. 1, 218-21 (1992).
Corder, E. et al., Science, vol. 261, 921-23 (1993).
Sherrington, R. et al., Nature, vol. 375, 754-60 (1995).
Kamino, K. et al., Neuroscience Letters, vol. 208, 195-98 (1996).

(Continued)

*Primary Examiner*—Deborah Crouch
(74) *Attorney, Agent, or Firm*—Greenblum & Bernstein, P.L.C.

(57) ABSTRACT

A gene-mutated animal such as a mouse which comprises a mutant prsenilin-1 gene comprising a DNA having a sequence encoding a mutant presenilin-1 protein in which an amino acid is substituted with a different amino acid in an amino acid sequence of a presenilin-1 protein; for example, a mutant presenilin protein in which isoleucine at position 213 is substituted with an amino acid other than isoleucine, e.g., threonine, in a mouse presenilin-1 protein. The animal is useful as an animal model which has pathological conditions closer to a human patient with Alzheimer's disease.

17 Claims, 8 Drawing Sheets

OTHER PUBLICATIONS

Hardy, J., TINS, vol. 20, 154-59 (1997).
Scheuner, D. et al., Nature Medicine, vol. 2, 864-70 (1996).
Xia, W. et al., J. Biolical Chemistry, vol. 272, 7977-82 (1997).
Borchelt, D. et al., Neuron, vol. 17, 1005-13 (1996).
Citron, M. et al., Nature Medicine, vol. 3, 67-72 (1997).
Lemere, C. et al., Nature Medicine, vol. 2, 1146-50 (1996).
Duff, K. et al., Nature, vol. 383, 710-13 (1996).
Levy-Lahad, E. et al., Science, vol. 269, 973-77 (1995).
Games, D. et al., Nature, vol. 373, 523-27 (1995).
Hsiao, K et al., Science, vol. 274, 99-102 (1996).
Sturchler-Pierrat, C. et al., PNAS, vol. 94, 13287-92 (1997).
Tybulewicz, V. et al., Cell, vol. 65, 1153-63 (1991).
Taniuchi, I. et al., EMBO, vol. 14, 3664-78 (1995).
Sakai, K. and Miyazaki, J., Biochem. Biophys. Res. Commun., vol. 237, 318-24 (1997).
Yamamura, K., "Byoutari seiri", vol. 14, 961-66 (1995).
English Language excerpt of Section 3, "Heterogeneity of AB Species", of Tamaoka, A., *Internal Medicine*, vol. 77, pp. 843-851 (1996).
Yuka Nakano et al., "Short Communication: Accumulation of Murine Amyloid$\beta$42 in a Gene-Dosage-Dependent Manner in PS1 'Knock-In' Mice", European Journal of Neuroscience, vol. 11, pp. 2577-2581 (1999).
K. S. Dorfman et al., Society for Neuroscience Abstracts, vol. 24, nr. 1 / 2. p. 472, XP-001062973.
A.G. Reaume et al., Journal of Biological Chemistry, vol. 271, No. 38, pp. 23380-23388.
Betz et al., "Bypass of lethality with mosaic mice generated by Cre-IoxP-mediated recombination," Current Biology, vol. 6, No. 10, pp. 1307-1316, 1996.
Mattson et al., "The Presenilins," The Neuroscientist, vol. 5, No. 2, 112-124, 1999.
Baudoin et al., "Knockout and knockin of the $\beta$1 exon D define distinct roles for integrin splice variants in heart function and embryonic development," Genes & Development, 12:1202-1216, 1998.
Shastry, "Gene disruption in mice: Models of development and disease," Molecular and Cellular Biochemistry, 181: 163-179, 1998.

* cited by examiner

SEQUENCE LISTING

```
<160> NUMBER OF SEQ ID NOS: 22

<210> SEQ ID NO 1
<211> LENGTH: 467
<212> TYPE: PRT
<213> ORGANISM: Human

<400> SEQUENCE: 1

Met Thr Glu Leu Pro Ala Asx Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
        195                 200                 205

Gly Met Ile Ser Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255
```

```
Asp Leu Asp Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
            275                 280                 285

Ser Ser Thr Met Val Trp Leu Val Asn Met Ala Glu Gly Asp Pro Glu
            290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
            325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
            355                 360                 365

Leu Ala Gly Glu Asp Pro Glu Glu Arg Gly Val Lys Leu Gly Leu Gly
            370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
            405                 410                 415

Gly Leu Cys Leu Thr Leu Leu Leu Ala Ile Phe Lys Lys Ala Leu
            420                 425                 430

Pro Ala Leu Pro Ile Ser Ile Thr Phe Gly Leu Val Phe Tyr Phe Ala
            435                 440                 445

Thr Asp Tyr Leu Val Gln Pro Phe Met Asp Gln Leu Ala Phe His Gln
            450                 455                 460

Phe Tyr Ile
465

<210> SEQ ID NO 2
<211> LENGTH: 1404
<212> TYPE: DNA
<213> ORGANISM: Human

<400> SEQUENCE: 2
atgacagagt acctgcacc gttgtcctac ttccagaatg cacagatgtc tgaggacaac      60
cacctgagca atactgtacg tagccagaat gacaatagag aacggcagga gcacaacgac    120
agacggagcc ttggccaccc tgagccatta tctaatggac gaccccaggg taactcccgg    180
caggtggtgg agcaagatga ggaagaagat gaggagctga cattgaaata tggcgccaag    240
catgtgatca tgctctttgt ccctgtgact ctctgcatgg tggtggtcgt ggctactatt    300
aagtcagtca gcttttatac ccggaaggat gggcagctaa tctataccccc attcacagaa    360
gataccgaga ctgtgggcca gagagccctg cactcaattc tgaatgctgc catcatgatc    420
agtgtcattg ttgtcatgac tatcctcctg gtggttctgt ataaatacag gtgctataag    480
gtcatccatg cctggcttat tatatcatct ctattgttgc tgttcttttt ttcattcatt    540
tacttgggg aagtgtttaa aacctataac gttgctgtgg actacattac tgttgcactc    600
ctgatctgga ttttggtgt ggtgggaatg atttccattc actggaaagg tccacttcga    660
ctccagcagg catatctcat tatgattagt gccctcatgg ccctggtgtt tatcaagtac    720
ctccctgaat ggactgcgtg gctcatcttg gctgtgattt cagtatatga tttagtggct    780
gttttgtgtc cgaaaggtcc acttcgtatg ctggttgaaa cagctcagga gagaaatgaa    840
```

```
acgcttttc cagctctcat ttactcctca acaatggtgt ggttggtgaa tatggcagaa    900
ggagacccgg aagctcaaag gagagtatcc aaaaattcca agtataatgc agaaagcaca    960
gaaagggagt cacaagacac tgttgcagag aatgatgatg gcgggttcag tgaggaatgg   1020
gaagcccaga gggacagtca tctagggcct catcgctcta cacctgagtc acgagctgct   1080
gtccaggaac tttccagcag tatcctcgct ggtgaagacc cagaggaaag gggagtaaaa   1140
cttggattgg gagatttcat tttctacagt gttctggttg gtaaagcctc agcaacagcc   1200
agtggagact ggaacacaac catagcctgt ttcgtagcca tattaattgg tttgtgcctt   1260
acattattac tccttgccat tttcaagaaa gcattgccag ctcttccaat ctccatcacc   1320
tttgggcttg ttttctactt tgccacagat tatcttgtac agccttttat ggaccaatta   1380
gcattccatc aattttatat ctag                                         1404
```

<210> SEQ ID NO 3
<211> LENGTH: 467
<212> TYPE: PRT
<213> ORGANISM: Mouse

<400> SEQUENCE: 3

```
Met Thr Glu Ile Pro Ala Pro Leu Ser Tyr Phe Gln Asn Ala Gln Met
1               5                   10                  15

Ser Glu Asp Ser His Ser Ser Ala Ile Arg Ser Gln Asn Asp Ser
            20                  25                  30

Glu Glu Arg Gln Gln Gln His Asp Arg Gln Arg Leu Asp Asn Pro Glu
        35                  40                  45

Pro Ile Ser Asn Gly Arg Pro Gln Ser Asn Ser Arg Gln Val Val Glu
    50                  55                  60

Gln Asp Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Ile Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Val Thr Val Ala Leu Leu Ile Trp Asn Phe Gly Val Val
        195                 200                 205

Gly Met Ile Ala Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270
```

-continued

```
Glu Thr Ala Gln Glu Arg Asn Glu Thr Leu Phe Pro Ala Leu Ile Tyr
            275                 280                 285

Ser Ser Thr Met Val Trp Leu Val Asn Met Ala Glu Gly Asp Pro Glu
    290                 295                 300

Ala Glu Arg Arg Val Pro Lys Asn Pro Lys Tyr Asn Thr Gln Arg Ala
305                 310                 315                 320

Glu Arg Glu Thr Gln Asp Ser Gly Ser Gly Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Gly Ser Ile
        355                 360                 365

Leu Thr Ser Glu Asp Pro Glu Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Ala Ile Phe Lys Lys Ala Leu
            420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
    450                 455                 460

Phe Tyr Ile
465

<210> SEQ ID NO 4
<211> LENGTH: 1404
<212> TYPE: DNA
<213> ORGANISM: Mouse

<400> SEQUENCE: 4
atgacagaga tacctgcacc tttgtcctac ttccagaatg cccagatgtc tgaggacagc      60
cactccagca gcgccatccg gagccagaat gacagccaag aacggcagca gcagcatgac     120
aggcagagac ttgacaaccc tgagccaata tctaatgggc ggccccagag taactcaaga     180
caggtggtgg aacaagatga ggaggaagac gaagagctga cattgaaata tggagccaag     240
catgtcatca tgctctttgt ccccgtgacc ctctgcatgg tcgtcgtcgt ggccaccatc     300
aaatcagtca gcttctatac ccggaaggac ggtcagctaa tctacacccc attcacagaa     360
gacactgaga ctgtaggcca agagccctg cactcgatcc tgaatgcggc catcatgatc     420
agtgtcattg tcattatgac catcctcctg gtggtcctgt ataaatacag gtgctacaag     480
gtcatccacg cctggcttat tatttcatct ctgttgttgc tgttcttttt ttcgttcatt     540
tacttagggg aagtatttaa gacctacaat gtcgccgtgg actacgttac agtagcactc     600
ctaatctgga ttttggtgt ggtcgggatg attgccatcc actggaaagg ccccttcga      660 ctgcagcagg cgtatctcat tatgatcagt gccctcatgg ccctggtatt tatcaagtac     720
ctccccgaat ggaccgcatg gctcatcttg gctgtgattt cagtatatga tttggtggct     780
gttttatgtc ccaaaggccc acttcgtatg ctggttgaaa cagctcagga agaaatgag      840 actctctttc cagctcttat ctattcctca caatggtgt ggttggtgaa atgggctgaa      900
ggagacccag aagcccaaag gagggtaccc aagaacccca gtataacac acaaagagcg     960
```

```
gagagagaga cacaggacag tggttctggg aacgatgatg gtggcttcag tgaggagtgg      1020
gaggcccaaa gagacagtca cctggggcct catcgctcca ctcccgagtc aagagctgct      1080
gtccaggaac tttctgggag cattctaacg agtgaagacc cggaggaaag aggagtaaaa      1140
cttggactgg gagatttcat tttctacagt gttctggttg gtaaggcctc agcaaccgcc      1200
agtggagact ggaacacaac catagcctgc tttgtagcca tactgatcgg cctgtgcctt      1260
acattactcc tgctcgccat tttcaagaaa gcgttgccag ccctcccat ctccatcacc       1320 ttcgggctcg tgttctactt cgccacggat taccttgtgc agcccttcat ggaccaactt      1380
gcattccatc agttttatat ctag                                             1404
```

<210> SEQ ID NO 5
<211> LENGTH: 25
<212> TYPE: DNA
<213> ORGANISM: Artificial
<220> FEATURE:
<223> OTHER INFORMATION: Primer

<400> SEQUENCE: 5
ggaattttgg tgtggtcggg atgat                                              25

<210> SEQ ID NO 6
<211> LENGTH: 23
<212> TYPE: DNA
<213> ORGANISM: Artificial
<220> FEATURE:
<223> OTHER INFORMATION: Primer

<400> SEQUENCE: 6
ggtccattcg gggaggtact tga                                                23

<210> SEQ ID NO 7
<211> LENGTH: 36
<212> TYPE: DNA
<213> ORGANISM: Artificial
<220> FEATURE:
<223> OTHER INFORMATION: Primer

<400> SEQUENCE: 7
tgtggtcggg atgatcgcca cccactggaa aggccc                                  36

<210> SEQ ID NO 8
<211> LENGTH: 36
<212> TYPE: DNA
<213> ORGANISM: Artificial
<220> FEATURE:
<223> OTHER INFORMATION: Primer

<400> SEQUENCE: 8
gggcctttcc agtgggtggc gatcatcccg accaca                                  36

<210> SEQ ID NO 9
<211> LENGTH: 18
<212> TYPE: DNA
<213> ORGANISM: Artificial
<220> FEATURE:
<223> OTHER INFORMATION: Primer

<400> SEQUENCE: 9
tctagacggc cgtctaga                                                      18

<210> SEQ ID NO 10
<211> LENGTH: 18

-continued

```
<212> TYPE: DNA
<213> ORGANISM: Artificial
<220> FEATURE:
<223> OTHER INFORMATION: Primer

<400> SEQUENCE: 10
agatctgccg gcagatct                                                    18

<210> SEQ ID NO 11
<211> LENGTH: 30
<212> TYPE: DNA
<213> ORGANISM: Artificial
<220> FEATURE:
<223> OTHER INFORMATION: Primer

<400> SEQUENCE: 11
cccaactcta tttctaccct cgttcatctg                                       30

<210> SEQ ID NO 12
<211> LENGTH: 30
<212> TYPE: DNA
<213> ORGANISM: Artificial
<220> FEATURE:
<223> OTHER INFORMATION: Primer

<400> SEQUENCE: 12
tagtgagacg tgctacttcc atttgtcacg                                       30

<210> SEQ ID NO 13
<211> LENGTH: 30
<212> TYPE: DNA
<213> ORGANISM: Artificial
<220> FEATURE:
<223> OTHER INFORMATION: Primer

<400> SEQUENCE: 13
tgctggagga aaatgtgtta tttaagagca                                       30

<210> SEQ ID NO 14
<211> LENGTH: 30
<212> TYPE: DNA
<213> ORGANISM: Artificial
<220> FEATURE:
<223> OTHER INFORMATION: Primer

<400> SEQUENCE: 14
tactgaaatc acagccaaga tgagccatgc                                       30

<210> SEQ ID NO 15
<211> LENGTH: 30
<212> TYPE: DNA
<213> ORGANISM: Artificial
<220> FEATURE:
<223> OTHER INFORMATION: Primer

<400> SEQUENCE: 15
ggtccatccc agcttcacac agacaagtct                                       30

<210> SEQ ID NO 16
<211> LENGTH: 30
<212> TYPE: DNA
<213> ORGANISM: Artificial
<220> FEATURE:
<223> OTHER INFORMATION: Primer

<400> SEQUENCE: 16
```

```
tactgaaatc acagccaaga tgagccatgc                                           30
```

<210> SEQ ID NO 17
<211> LENGTH: 30
<212> TYPE: DNA
<213> ORGANISM: Artificial
<220> FEATURE:
<223> OTHER INFORMATION: Primer

<400> SEQUENCE: 17

```
tagtgagacg tgctacttcc atttgtcacg                                           30
```

<210> SEQ ID NO 18
<211> LENGTH: 36
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (16)..(16)
<223> OTHER INFORMATION: y is t or c
<220> FEATURE:
<221> NAME/KEY: misc_feature
<222> LOCATION: (20)..(22)
<223> OTHER INFORMATION: wherein v is a base other than t; and wherein
      avc represents a codon, as triplet bases of a mutant presenilin-1
      gene, encoding an amino acid.

<400> SEQUENCE: 18

```
tgtggtcggg atgatygcca vccactggaa aggccc                                    36
```

<210> SEQ ID NO 19
<211> LENGTH: 36
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (16)..(16)
<223> OTHER INFORMATION: y is t or c
<220> FEATURE:
<221> NAME/KEY: misc_feature
<222> LOCATION: (20)..(22)
<223> OTHER INFORMATION: wherein acc represents a codon, as triplet
      bases of a mutant presenilin-1 gene, encoding an amino acid.

<400> SEQUENCE: 19

```
tgtggtcggg atgatygcca cccactggaa aggccc                                    36
```

<210> SEQ ID NO 20
<211> LENGTH: 36
<212> TYPE: DNA
<213> ORGANISM: Artificial
<220> FEATURE:
<223> OTHER INFORMATION: synthetic construct
<220> FEATURE:
<221> NAME/KEY: misc_feature
<222> LOCATION: (16)..(16)
<223> OTHER INFORMATION: y is t or c
<220> FEATURE:
<221> NAME/KEY: misc_feature
<222> LOCATION: (20)..(22)
<223> OTHER INFORMATION: wherein each n is independently chosen from any
      base; and nnn represents a codon, as triplet bases of a mutant
      presenilin-1 gene, encoding an amino acid other than isoleucine.

<400> SEQUENCE: 20

```
tgtggtcggg atgatygccn nncactggaa aggccc                                    36
```

```
<210> SEQ ID NO 21
<211> LENGTH: 12
<212> TYPE: DNA
<213> ORGANISM: Artificial
<220> FEATURE:
<223> OTHER INFORMATION: oligodeoxynucleotide targeting vector

<400> SEQUENCE: 21
ctagacggcc gt                                                          12

<210> SEQ ID NO 22
<211> LENGTH: 18
<212> TYPE: DNA
<213> ORGANISM: Artificial
<220> FEATURE:
<223> OTHER INFORMATION: vector

<400> SEQUENCE: 22
tctagacggc cgtctaga                                                    18
```

KNOCKIN GENE-MUTATED MOUSE COMPRISING A MUTANT PRESENILIN-1 GENE

FIELD OF THE INVENTION

This invention relates to a trans-genic animal. More specifically, the invention relates to a presenilin trans-genic animal with a transferred mutated presenilin gene causing human Alzheimer's disease.

BACKGROUND OF THE INVENTION

Alzheimer's disease exhibits a symptom of progressive dementia. Its pathologic histology is characterized by emergence of a huge number of senile plaques in the brain and accumulation of neurofibrillary degenerations in neurons. The disease is neurodegenerative in which neurons are gradually leading to deciduation. Alzheimer's disease generally develops in old age and its prevalence is known to increase with aging. At present, a definitive treatment of Alzheimer's disease is impossible. Accordingly, in order to prepare for sharp increase of the old age population in the future, early developments of a method of therapeutic and preventive treatment of Alzheimer's disease and an effective medicament for preventive and therapeutic treatment of the disease are desired.

Senile plaque is a deposit outside neurons which contains various ingredients, and whose main ingredient is a peptide consisting of 39–42 amino acid residues called amyloid β protein (Aβ). Amyloid precursor protein (APP) is cleaved by proteases tentatively named β secretase and γ secretase to produce amyloid β. In the senile plaque, the amyloid β deposits as a rigid construct having β sheet structure. The senile plaque is first formed as a "stain-like" deposition called as a diffuse senile plaque. At this stage, neurodegeneration has not yet occurred. It is considered that, as the diffuse senile plaque becomes a more rigid deposition, the degeneration or deciduation of neurocytes occurs, which results in the onset of symptoms of Alzheimer's disease such as dementia. There are Aβ 40 consisting of 40 amino acid residues and Aβ 42 consisting of 42 amino acid residues as main amyloid β. Most of amyloid β generated by cells is Aβ 40, and only a little amount of Aβ 42 exists. However, Aβ 42 has higher aggregation properties, and therefore, Aβ42 is considered to have a more significant role than Aβ 40 in the formation of senile plaque (Tamaoka, Naika (Internal Medicine), Vol. 77, P843, 1996).

In Alzheimer's disease, familial onsets are observed which exhibit an autosomal dominant inheritance. A gene first identified as a causal gene of the familial onset of Alzheimer's disease in 1991 is a mutant of APP, a gene located on chromosome 21 in which amino acid residue at position 717 is mutated from valine to isoleucine (Goate A. et al., Nature, Vol. 349, P704, 1991).

Other mutants of APP as causes of Alzheimer's disease were found such as those where said amino acid residue at position 717 is mutated to phenylalanine (Murrell J. et al., Science, Vol. 254, P97, 1991); where the amino acid residue at the same position is mutated to glycin (Chartier, Harlin et al., Nature, Vol. 353, P844, 1991); where two amino acid residues at positions 670 and 671 are mutated from lysine-methionine to asparagine-leucine (Mullan M. et al., Nature Genet., Vol. 1, P345, 1992); and where amino acid residue at position 692 is mutated from alanine to glycin (Hendrisk L. et al., Nature Genet., Vol. 1, P218, 1992) and the like.

Apolipoprotein E (apo E) was reported in 1993 as a causal factor or a risk factor of the familial Alzheimer's disease. Persons with Alzheimer's disease were found to have apoE4, in which the amino acid residue at position 112 is arginine and the amino acid residue at position 158 is arginine, at a significantly higher rate than healthy persons among isomers of apoE whose genes are located on chromosome 19 (Corder E. H. et al., Science, Vole 261, P921, 1993).

After then, a mutant of the gene "presenilin-1" (PS-1, initially called as S182) being located on chromosome 14 (Sherrington R. et al., Nature, Vol. 375, P754, 1995) and a mutant of the gene "presenilin-2" (PS-2, initially called as E5-1 or STM-2) being located on chromosome 1 (Sherrington R. et al., Nature, Vol. 375, P754, 1995) were found as new causal genes for Alzheimer's disease in 1995 (in the specification, each gene is called as "presenilin-1 gene" and "presenilin-2 gene", respectively, and each gene product is called as "presenilin-1 protein" and "presenilin-2 protein", or "PS-1" and "PS-2", respectively.)

Presenilin-1 protein and presenilin-2 protein consisting respectively of 467 and 448 amino acid residues have a seven (or eight)-fold transmembrane primary structure, and accordingly, they are presumably present as membrane proteins. Homology of the two proteins is high at amino acids level, i.e., 67% in total and 84% in the transmembrane domain alone. As for function of presenilin-1 protein, the protein is suggested to possibly have similar functions to nematode sel-12 protein or SPE-4 protein because of high homology to these proteins. SPE-4 protein participates in nematode spermatogenesis process and is considered to be involved in transport and storage of proteins.

Consequently, presenilin-1 protein is believed to participate possibly in processing of membrane proteins such as APP, axoplasmic transport, and fusion of membrane vesicle with membranes. The sel-12 was found as a gene which remedies an embryological abnormality caused by mutation of lin-12 which controls nematode development. The lin-12 is considered to be involved in intercellular signal transduction, and accordingly, presenilin-1 protein is also suggested to possibly participate in a certain step of intercellular signal transduction.

The first report on presenilin-1 protein describes that mutations causing the familial Alzheimer's disease are substitutions of amino acid residues at five positions. After this report, genes mutated at various sites were found from many families afflicted with familial Alzheimer's disease, which include OS-2 (isoleucine at position 213 is mutated to threonine) and OS-3 (valine at position 96 is mutated to phenylalanine), both reported by the present inventors (Kamino K. et al., Neurosci., Lett., Vol. 208, P195, 1996), and more than 40 types of amino acid substitutions have been known at more than 30 sites so far (Hardy. TINS, Vol. 20, P154, 1997).

At present, 70–80% of the familial Alzheimer's disease is believed to be related to the mutation of presenilin-1 protein. Mutations at two sites have been reported as for presenilin-2 protein. As explained above, genetic analysis has proved that mutants of presenilin-1 and presenilin-2 proteins are deeply involved in the familial Alzheimer's disease.

Studies on mechanism how the mutants of presenilin-1 and presenilin-2 proteins cause the onset of Alzheimer's disease have also been progressed. It has been reported that Aβ 40 is almost the same level as normal presenilin-1 and presenilin-2 proteins, whilst Aβ 42 is highly increased as compared to normal presenilin-1 and presenilin-2 proteins in serum or a culture medium of dermal fibroblasts from a patient with Alzheimer's disease having the aforementioned mutants (Scheuner D. et al.: Nature Med., Vol. 2, P864, 1996); in a culture medium of a cell line transformed by mutants of presenilin-1 protein and presenilin-2 protein (Xia W. et al.: J. Biol. Chem. Vol. 272, P7977, 1997; Borchelt D. R. et al.: Neuron, Vol. 17, P1005, 1996; Citron, M. et al.: Nature Med., Vol. 3, P67, 1997); and in the brain tissue of a patient with familial Alzheimer's disease having the mutant presenilin-1 protein (Lemere C. A. et al.: Nature Med., Vol. 2., P1146, 1996).

These reports show that the mutants of presenilin-1 protein and presenilin-2 protein, which cause the familial Alzheimer's disease, possibly trigger the onset of Alzheimer's disease by the increase of A β'42 which is considered to play a significant role in the formation of senile plaque. A trans-genic mouse transferred with a gene encoding the mutant presenilin-1 protein was created (Duff K. et al.: Nature, Vol. 383, P710, 1996, Borchelt D R. et al.: Neuron, Vol. 17, P1005, 1996 and Citron M. et al.: Nature Med., Vol. 3, P67, 1997). It was reported that Aβ 42 in the brain of the trans-genic mouse selectively increased. These results are strong supports of the possibility that mutants of presenilin-1 protein and presenilin-2 protein causing the familial Alzheimer's disease increase Aβ 42 which possibly has significant roles in the formation of senile plaque, thereby develop Alzheimer's disease. However, no description is given about histological study of the mouse's brain in the above reports on the trans-genic mouse, which presumably due to no observation of remarkable histological change in the brain of the trans-genic mouse.

Generally, trans-genic animals are useful as a means of analyzing functions of a target gene in vivo. However, it is technically difficult to control the expression of a transferred gene quantitatively, tissue specifically, or time specifically during development. There is also a problem in that two different gene products are present as a mixture in the trans-genic animals since a gene inherently possessed by the animal still works for normal expression, and functions of a transferred gene cannot be sufficiently analyzed. Furthermore, when the transferred gene is subjected to particularly excessive expression, functions not inherently performed in vivo may appear in trans-genic animals, which results in a defect of possible confusion in analysis of constructed gene-mutated animals.

Apart from trans-genic animals, knockout animals may also be used as a means of analyzing functions of a target gene. In a knockout animal, a target gene inherently possessed by the animal is artificially destroyed so as to be dysfunctional. A detailed analysis of knockout animals may reveal functions of a target gene in vivo. However, particular changes in knockout animals created as homozygote sometimes fails to appear, since the functions of the other gene products in the knockout animal may substitute for that of the destroyed gene products. Furthermore, there is also a problem in that an animal as homozygote may sometimes be lethal because the destroyed gene product is essential to the animal's development and growth, whilst thorough analysis of gene functions of an animal as viable heterozygote is practically impossible.

DISCLOSURE OF THE INVENTION

An object of the present invention is to provide, for creation of an animal pathologic model of Alzheimer's disease, an animal as a pathological model whose pathologic conditions is closer to those of a patient with Alzheimer's disease, instead of a trans-genic animal having the aforementioned defects. More specifically, the object of the present invention is to provide a gene-mutated animal capable of expressing a mutant presenilin protein in the brain by transfer of a mutant of a presenilin gene which is believed to be a causal gene of Alzheimer's disease (a mutant presenilin gene) according to a homologous recombination technique. Further objects of the present invention are to provide a method of producing said gene-mutated animal; a plasmid useful for the aforementioned production method; and a method for evaluating a substance or an agent effective for preventive and/or therapeutic treatment of Alzheimer's disease using the aforementioned gene-mutated animal.

In order to reveal roles of presenilin-1 protein and mechanism of the onset of Alzheimer's disease by the mutation of presenilin-1 gene, the inventors of the present invention created a knockin mouse in which presenilin-1 gene inherently possessed by the mouse is replaced with the aforementioned presenilin-1 gene with OS-2 type mutation. As a result, the inventors found that the gene-mutated mouse successfully avoided the defects with the trans-genic mice and the knockout mice, and that the animal was useful for investigations of cause and pathology of familial Alzheimer's disease caused by the mutant presenilin-1 gene. The inventors further continued the research, and achieved the present invention set out below.

The present invention thus provides a non-human gene-mutated animal having a mutant presenilin-1 gene, and more preferably, the invention provides a gene-mutated animal having a mutant presenilin-1 gene which comprises a DNA having a sequence encoding a presenilin-1 protein in which an amino acid in an amino acid sequence of a presenilin-1 protein is substituted with a different amino acid.

The present invention also provides:

a non-human gene-mutated animal having a mutant presenilin-1 gene which comprises a DNA having a sequence encoding a mutant presenilin-1 protein which has an amino acid sequence in which one or more amino acids at positions selected from the group consisting of amino acid numbers 79, 82, 96, 115, 120, 135, 139, 143, 146, 163, 209, 213, 231, 235, 246, 250, 260, 263, 264, 267, 269, 280, 285, 286, 290, 318, 384, 392, 410, 426, and 436 is substituted with different amino acid(s) in an amino acid sequences of a presenilin-1 protein, preferably a mouse-derived presenilin-1 protein; and a non-human gene-mutated animal having a mutant presenilin-1 gene which comprises a DNA having a sequence encoding a mutant presenilin-1 protein which has one or more mutations selected from the group consisting of A79V, V82L, V96F, Y115H, Y115C, E120K, E120D, N135D, M139V, M139T, M139I, I143F, I143T, M146L, M146V, H163Y, H163R, G209V, I213T, A231T, A231V, L235P, A246E, L250S, A260V, C263R, P264L, P267S, R269G, R269G, R269H, E280A, E280G, A285V, L286V, S290C, E318G, G384A, L392V, C410Y, A426P and P436S in an amino acid sequence of a presenilin-1 protein, more preferably a mouse presenilin-1 protein (Each alphabet represents an amino acid expressed as a one-letter symbol, each number represents an amino acid number from the N-terminus of the presenilin-1 protein, and the descriptions mean that a wild-type amino acid shown in the left of the numerical figure is substituted with an amino acid shown in the right. In the specification, mutant presenilin-1 protein and mutant presenilin-2 protein are shown in the same manner.).

The present invention further provides a non-human gene-mutated animal having a mutant presenilin-1 gene which comprises a DNA having a sequence encoding a mutant presenilin-1 protein in which isoleucine at position 213 of a presenilin-1 protein is substituted with an amino acid other than isoleucine, and a non-human gene-mutated animal having a mutant presenilin-1 gene which comprises a DNA having a sequence encoding a mutant presenilin-1 protein in which isoleucine at position 213 of a presenilin-1 protein is substituted with threonine.

According to preferred embodiments of the aforementioned inventions, there are provided:

the aforementioned gene-mutated animal having a mutant presenilin-1 gene wherein a DNA sequence encoding around an amino acid at position 213 in an amino acid sequence of a presenilin-1 protein is mutated to the following sequence:

5'-TGTGGTCGGGATGATYGCC AVC CACTGGAAAG-GCCC-3' (SEQ ID NO: 18)

wherein V represents a base other than T, Y represents T or C, and the underlined bases encode the amino acid at position 213;

the aforementioned gene-mutated animal having a mutant presenilin-1 gene wherein a DNA sequence encoding around an amino acid at position 213 in an amino acid sequence of a presenilin-1 protein is mutated to the following sequence:

5'-TGTGGTCGGGATGATYGCC ACCCACTGGAAAGGCCC-3' (SEQ ID NO: 19)

wherein Y represents T or C, and the underlined bases encode the amino acid at position 213; and the aforementioned gene-mutated animal having a mutant presenilin-1 gene wherein a DNA sequence encoding around an amino acid at position 213 in an amino acid sequence of a presenilin-1 protein is mutated to the following sequence:

5'-TGTGGTCGGGATGATYGCC NNNCACTGGAAAGGCCC-3' (SEQ ID NO: 20)

wherein each N independently represents A G, T or C and NNN represents a codon as triplet bases which encodes an amino acids other than isoleucine, Y represents T or C, and the underlined bases encode the amino acid at position 213.

From another aspect, the present invention provides a non-human gene-mutated animal having a mutant presenilin-2 gene which comprises a DNA having a sequence encoding a protein in which an amino acid at position 141 and/or 436 is substituted with a different amino acid in an amino acid sequence of a presenilin-2 protein. As a preferred embodiment of the invention, there is provided the aforementioned non-human gene-mutated animal wherein the mutant presenilin-2 gene comprises a DNA having a sequence encoding a mutant presenilin-2 protein which contains a mutation of N141I and/or M239V in an amino acid sequence of a presenilin-2 protein.

As preferred embodiments of the aforementioned gene-mutated animals, the present invention provides the aforementioned gene-mutated animal wherein overexpression of amyloid β protein is caused by the mutant presenilin-1 gene and/or the mutant presenilin-2 gene; the aforementioned gene-mutated animal which can express the mutant presenilin protein and wherein the expression of said protein induces the production of amyloid β protein in an amount sufficient to form a progressive neural disease in a peripheral portion of the cerebral cortex of the brain of the animal; the aforementioned gene-mutated animal wherein the animal is a rodent, preferably a mouse; the aforementioned gene-mutated animal wherein the aforementioned mutant presenilin-1 gene and/or the aforementioned mutant presenilin-2 gene are transferred by homologous recombination; the aforementioned gene-mutated animal wherein amount of the amyloid protein expression in a brain tissue induced by the aforementioned presenilin-1 gene is sufficient to cause affected behavior in a memory learning test in comparison with a normal animal, and to induce abnormal neuropathy in a peripheral portion of the cerebral cortex of the hippocampus of the brain of the animal; and the non-human gene-mutated animal having a DNA which comprises a mutant preceilin-1 gene encoding a mutant preceilin-1 protein in which one or two or more amino acids is substituted with a different amino acid in the amino acid sequence of the presenilin-1 protein together with a DNA having a nucleotide sequence encoding a marker protein.

From further aspect, the present invention provides a plasmid comprising a DNA having a sequence of a mutant presenilin-1 gene wherein a DNA sequence encoding around an amino acid at position 213 of a presenilin-1 protein is the following sequence:

5'-TGTGGTCGGGATGATYGCC AVC CACTGGAAAG-GCCC-3' (SEQ ID NO: 18)

wherein V represents A, G, or C, Y represents T or C, and the underlined bases encode an amino acid at position 213; and a plasmid comprising a DNA having a sequence of a mutant presenilin-1 gene which encodes a mutant presenilin-1 protein wherein an amino acid at position 213 is substituted with an amino acid other than isoleucine in an amino acid sequence of the presenilin-1 protein and a DNA sequence encoding around the amino acid at position 213 of presenilin-1 protein is the following sequence:

5'-TGTGGTCGGGATGATYGCC NNN CACTGGAAAG-GCCC-3' (SEQ ID NO: 20)

wherein Y represents T or C, each N independently represents A, G, T, or C and NNN represents a codon as triplet bases encoding an amino acid other than isoleucine, and the underlined bases encode the amino acid at position 213. Additionally, the present invention also provides a chromosomal DNA containing exon 8 of a mutant presenilin-1 gene encoding a mutant presenilin-1 protein wherein an amino acid at position 213 is substituted with an amino acid other than isoleucine in an amino acid sequence of a presenilin-1 protein.

Furthermore, the present invention provides a plasmid comprising a DNA wherein a Sau3AI site is introduced into a nucleotide sequence comprising the whole or a mutated part of a cDNA or chromosomal DNA of a mutant presenilin-1 gene encoding a mutant presenilin-1 protein in which an amino acid at position 213 is substituted with an amino acid other than isoleucine in an amino acid sequence of presenilin-1 protein. Also provided are the aforementioned plasmid wherein the substitution of the amino acid is isoleucine at position 213 with threonine; and a plasmid comprising a DNA specified by the following nucleotide sequence:

5'-TGTGGTCGGGATGATYGCCACCCACTG-GAAAGGCCC-3' (SEQ ID NO: 19)

wherein Y represents T or C.

In addition to the above inventions, the present invention also provides a gene encoding a mouse mutant presenilin-1 protein wherein isoleucine at position 213 is substituted with an amino acid other than isoleucine in an amino acid sequence of a mouse presenilin-1 protein; and the aforementioned gene wherein the substitution is from isoleucine to threonine. Also provided are a plasmid comprising: (1) a gene encoding a mouse mutant presenilin-1 protein wherein isoleucine at position 213 is substituted with an amino acid other than isoleucine in an amino acid sequence of a mouse presenilin-1 protein; and (2) a neomycine expression unit flanked by loxPs; and the aforementioned plasmid wherein the substitution is from isoleucine to threonine (loxP has been disclosed in Japanese Patent Laid-Open Publication (Kohyo) No. 4-501501, page 4).

From further aspect, the present invention provides an embryo introduced with a plasmid comprising a DNA represented by the nucleotide sequence:
5'-TGTGGTCGGGATGATYGCCACCCACTG-GAAAGGCCC-3' (SEQ ID NO: 19) wherein Y represents T or C; an embryo obtained by homologous recombination using each of the aforementioned plasmids; and the aforementioned embryo derived from a mammalian rodent, more preferably from a mouse. The invention also provides a primary cell culture or subcultured cell obtained by isolating a cell from the aforementioned gene-mutated animal and culturing the cell by tissue culture; a method for producing a non-human gene-mutated animal wherein the method comprises the step of transferring a mutant presenilin-1 gene by homologous recombination into an embryo of an animal, wherein the mutant presenilin-1 gene is capable of expressing the mutant presenilin-1 and inducing production of amyloid β protein in an amount sufficient to form a progressive neural disease in a peripheral portion of the cerebral cortex of the brain; and the aforementioned production method wherein a mutant presenilin-1 protein can be expressed wherein isoleucine at position 213 is substituted with an amino acid other than isoleucine.

Additionally, the invention provides a method for evaluating a substance useful for therapeutic and/or preventive treatment of Alzheimer's disease which comprises the step of subjecting the aforementioned gene-mutated animal which is administered with a test substance to a comparison with the gene-mutated animal not administered with the test compound. A typical example of the method for evaluation includes a screening method. According to preferred embodiments of the invention, there are provided the aforementioned method for evaluation wherein the comparison is conducted by using a memory learning test; the aforementioned method for evaluation wherein the comparison is conducted by using a pathological test; the aforementioned method for evaluation wherein the comparison is conducted by a pathological test based on neuropathology in a peripheral portion of the cerebral cortex; the aforementioned method for evaluation wherein the comparison conducted by the pathological test based on neuropathology is a comparison of one or more items selected from the group consisting of suppression of decrease in overgrown gliosis in a peripheral portion of the cerebral cortex of the brain, suppression of decrease in uptake of 2-deoxyglucose in a peripheral portion of the cerebral cortex of the brain, and suppression of decrease in availability of 2-deoxyglucose in the cerebral cortex of the brain; and the aforementioned method for evaluation wherein the comparison is conducted for one or more items selected from the group consisting of survival period of time, exploratory behavior and migratory behavior.

Still further, the present invention provides a method for evaluating a medicament for therapeutic and/or preventive treatment of Alzheimer's disease which comprises the step of culturing a primary cell culture or a subcultured cell in vitro in the presence of a test compound; a method for diagnosing Alzheimer's disease or a possibility of onset of Alzheimer's disease, which comprises the use of a partial nucleotide sequence of a mutant presenilin-1 gene encoding an OS-2 type mutant presenilin-1 protein; a substance useful for therapeutic and/or preventive treatment of Alzheimer's disease selected by each of the aforementioned evaluation methods; and a medicament for therapeutic and/or preventive treatment of Alzheimer's disease comprising the aforementioned substance as an active ingredient.

The present invention also provides a gene-mutated animal having a mutant presenilin gene and a gene encoding a mutant amyloid precursor protein, wherein the animal is a hybrid animal or its progeny which is produced by mating the aforementioned gene-mutated animal with an animal having a gene encoding a mutant protein of the amyloid precursor protein and a high productivity of amyloid β protein, and more preferably the animal is a hybrid mouse or its progeny which is produced by the mating or which is born as a result of the mating. According to a preferred embodiment of the invention, there is provided the aforementioned gene-mutated animal wherein the animal having a gene encoding a mutant protein of the amyloid precursor protein and a high productivity of amyloid β protein is a PS1-mutated mouse.

BEST MODE FOR CARRYING OUT THE INVENTION

Figure 1:
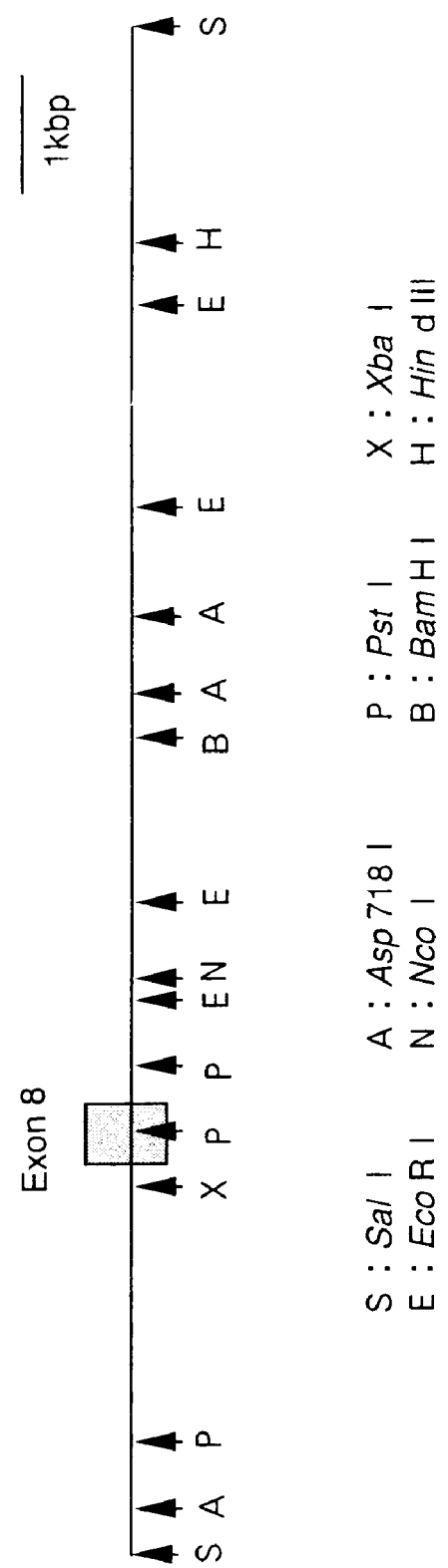
FIG. 1 is a restriction map of a chromosomal DNA fragment Pα containing exon 8 of mouse presenilin-1 which was obtained by cloning from a mouse genomic DNA library.

A mutant presenilin gene used in the production of the gene-mutated animal of the present invention is a gene encoding a mutant presenilin protein, and as used herein, "mutant presenilin gene" means either of, or both of a mutant presenilin-1 gene or a mutant presenilin-2 gene and "mutant presenilin protein" means either of, or both of a mutant presenilin-1 protein or a mutant presenilin-2 protein. The mutant presenilin gene has the property of increasing the production of amyloid β protein. The gene-mutated animal of the present invention is a mammal transferred with the above-mentioned mutant presenilin gene for example by homologous recombination. The mutation existing in the mutant protein is preferably a result of substitution of an amino acid residue. The number of mutations is not limited, and may preferably be 1.

The full length sequence of a mammal-derived preselin-1 protein is described in, for example, E. Levy-Lahad, et al., Science, 269, pp. 973–977, 1995. The full-length sequences of human and mouse presenilin-1 proteins and examples of DNA sequences that encode the proteins are shown in the sequence listings as SEQ ID NOS: 1 to 4. For example, in the mouse-derived presenilin-1, mutation sites may preferably be one or more sites selected from No. 79, No. 82, No. 96, No. 115, No. 120, No. 135, No. 139, No. 143, No. 146, No. 163, No. 209, No. 213, No. 231, No. 235, No. 246, No. 250, No. 260, No. 263, No. 264, No. 267, No. 269, No. 280, No. 285, No. 286, No. 290, No. 318, No. 384, No. 392, No. 410, No. 426, and No. 436.

More preferable mutations are one or more mutations selected from the group consisting of A79V, V82L, V96F, Y115H, Y115C, E120K, E120D, N135D, M139V, M139T, M139I, I143F, I143T, M146L, M146V, H163Y, H163R, G209V, I213T, A231T, A231V, L235P, A246E, L250S, A260V, C263R, P264L, P267S, R269G, R269G, R269H, E280A, E280G, A285V, L286V, S290C, E318G, G384A, L392V, C410Y, A426P, and P436S in the amino acid sequence of the presenilin-1 protein, more preferably in the amino acid sequence of the mouse-derived presenilin-1 protein. Among these mutations, the mutation wherein the amino acid at position 213 is substituted with another amino acid (referred to in some cases as "OS-2 type mutation" in the specification) is a particularly preferable mutation. For example, a mutation wherein isoleucine at position 213 is substituted with an amino acid other than isoleucine, or a mutation wherein isoleucine at position 213 is substituted with threonine is most preferable.

The full-length sequence of a mammal-derived preseline-2 protein is described in, for example, Science, 269, pp. 973–977, 1995. Position 141 and/or position 436 are preferable mutation sites, and in the mouse-derived sequence N141I and/or M239V are more preferable. One or more mutations may exist in either of presenilin-1 protein or presenilin-2 protein, or both of the proteins.

The gene-mutated animal of the present invention is characterized by having the above mutant presenilin-1 gene and/or mutant presenilin-2 gene on its chromosomal DNA. The gene-mutated animal is not limited so far that the animal is a mammal and a kind of the animal is not particularly limited. For example, a rodent may suitably be used. A mouse is particularly preferred. The gene-mutated animal of the present invention can be produced by constructing a plasmid using a DNA having a sequence of about 10 kbp comprising a mutant presenilin gene, and then transferring the plasmid into an embryonic stem cell and thereby causing homologous recombination intracellularly.

The gene-mutated animal of the present invention is characterized in that the amino acid mutation occurs mostly at only one position due to the transfer of the aforementioned mutant presenilin-1 and/or presenilin-2 gene by homologous recombination. In the case of a so-called "trans-genic animal", a DNA sequence comprising a mutant portion is inserted randomly into chromosomal DNA, and tens of copies of a repeated sequence are inserted at plural sites. The gene-mutated animal of the present invention can avoid the problems, and it is possible to accurately analyze pathology of Alzheimer's disease at genetic level. Where a DNA comprises a marker or the like is transferred to the gene-mutated animal of the present invention, the animal may have a site of the marker and a sequence for insertion of the marker. For example, for insertion at a site capable of being cleaved with Sau3AI, one nucleotide can be substituted, and such substitution can be verified by cleaving a PCR product with Sau3AI, followed by subjecting the fragments to electrophoresis or the like.

The gene-mutated animal of the present invention has a characteristic feature of producing amyloid β protein in a larger amount in comparison with a normal animal due to the genetic mutation. An increased amount of amyloid β protein achieved by the gene-mutated animal of the present invention is not particularly limited, and the amount may preferably be sufficient for recognition of a substantial difference in the evaluation of degrees of memory disorder, pathological observations, and various neural disorders as compared to a normal animal.

DNAs, plasmids, cell cultures, and embryos of mammalian cells provided by the present invention are characterized to have a mutant presenilin-1 gene and/or a mutant presenilin-2 gene. For example, a cDNA or a full-length chromosomal DNA of a mutant presenilin-1 gene encoding the mutant presenilin-1 protein, preferably an OS-2 type mutant presenilin-1 protein, or the DNA sequence comprising one or more mutation sites; a plasmid comprising a DNA being the above cDNA or full length chromosomal DNA, or the above DNA comprising one or more mutation sites, which is further introduced with an Sau3AI site; a chromosomal DNA comprising exon 8 of a mutant presenilin-1 gene encoding an OS-2 type mutant presenilin-1 protein fall within the present invention. Further, the present invention encompasses the above gene or the DNA which further comprises one or more, preferably 1 to 20, more preferably 1 to several substitutions of bases.

Examples of DNAs and plasmids of the present invention include, for example:

1) a DNA comprising a mutant presenilin-1 gene encoding a mutant presenilin-1 protein wherein isoleucine at position 213 of the presenilin-1 protein is substituted with threonine, or a plasmid comprising said DNA;

2) a DNA comprising a mutant presenilin-1 gene wherein a DNA nucleotide sequence encoding amino acids around position 213 of the amino acid sequence of a mutant presenilin-1 protein is the following sequence:
5'-TGTGGTCGGGATGAT Y GCCA V CCACTGGAAAG-GCCC-3' (SEQ ID NO: 18)

wherein V represents a nucleotide other than T and Y represents T or C, or a plasmid comprising said DNA;

3) a DNA comprising a mutant presenilin-1 gene wherein a DNA nucleotide sequence encoding amino acids around position 213 of the amino acid sequence of an OS-2 type mutant presenilin-1 protein is the following sequence:
5'-TGTGGTCGGGATGAT Y GCC NNN CACTG-GAAAGGCCC-3' (SEQ ID NO: 20)

wherein Y represents T or C, each N independently represents A, G, T, or C and NNN represents a codon as triplet bases encoding an amino acid other than isoleucine, or a plasmid comprising said DNA;

4) Any one of the DNAs or plasmids comprising said DNAs according to the aforementioned 1) to 4) wherein a Sau3AI restriction site is introduced;

5) a DNA or a plasmid comprising said DNA wherein a Sau3AI restriction site is introduced into a sequence comprising the full-length of a cDNA or a chromosomal DNA of a mutant presenilin-1 gene encoding a mutant presenilin-1 protein wherein isoleucine at position 213 is substituted with threonine in an amino acid sequence of presenilin-1 protein, or into a mutated portion of said sequence;

6) a DNA comprising exon 8 of a mutant mouse presenilin-1 gene encoding an OS-2 type mutant presenilin-1 protein and a neomycin expression unit flanked by loxP, or a plasmid comprising said DNA; and, 7) a DNA comprising exon 8 of a mutant presenilin-1 gene encoding a mutant presenilin-1 protein wherein isoleucine at position 213 is substituted with threonine in an amino acid sequence of presenilin-1 protein and a neomycin expression unit flanked by loxP, or a plasmid comprising said DNA. However, the scope of the invention is not limited to these specific examples:

The embryos or the cells provided by the present invention includes an embryo or a cell into which the above plasmid, e.g. a plasmid comprising a PRL-104 or PRL-105 nucleotide sequence is transferred. Preferable cells of the present invention include those transferred with a gene encoding a mutant presenilin protein which comprises a mutation at position 213 of the amino acid sequence of presenilin-1 protein by homologous recombination using the aforementioned plasmid. Sorts of the embryos or cells are not limited so far that they are derived from a mammal, and those derived from a rodent, preferably a mouse may be used.

Production of the Gene-Mutated Animal

After the DNA encoding a mutant of human presenilin is obtained, the presenilin gene mutated animal of the present invention can be produced according to the process described below. An example will be explained wherein a mouse is used as an mammal and the human mutant human presenilin-1 gene is used as the mutant human presenilin gene. However, the gene-mutated animal of the present invention is not limited to those produced by using these materials. Further, this method is one example of the method of production of the gene-mutated animal of the present invention and the method of the present invention is not limited to the following method. By referring to the general method described below and specific methods described in the examples, and by suitably modifying or altering these methods as required, a person skilled in the art can readily produce the gene-mutated animal of the present invention.

In order to prepare a probe for use in the PCR method, a DNA fragment, which comprises a site for mutation in exon 8 of a presenilin-1 gene deriving from an animal to be used for the production, is obtained from a mouse genomic DNA library. A mouse genomic DNA library of any strain may be used, including a mouse genomic library from mouse 129 strain described in the examples. Where a mouse is used as an animal for introduction of mutation, exon 8 of mouse presenilin-1 gene is used. Where other sort of animal is used, it is necessary to select an appropriate segment.

After of the DNA fragment prepared by the above process is labeled ($^{32}$P) by random priming, screening of the genomic library is performed using the labeled probe, and a chromosomal DNA fragment comprising exon 8 of the presenilin-1 gene is then cloned. A portion for mutation in exon 8 of the cloned presenilin-1 gene is further subcloned, and then a mutation is introduced.

A targeting vector is constructed which comprises the chromosomal DNA comprising exon 8 of the mouse presenilin-1 gene into which the mutation was introduced. As a selective marker, neo expression unit is introduced into the targeting vector to facilitate that cells whose chromosome is not introduced with the vector are killed by the addition of G418 (an antibiotic) to a medium. After the targeting vector is introduced into an ES cell by means of electroporation or by another method for gene transfer into a cell, the ES cells are cultured in the presence of G418 and colonies formed are collected. Each of the colonies obtained is divided into two portions. One portion is preserved by culturing, sub-culturing, or freezing. The other portion is used to investigate ES cells into which a desired mutation in exon 8 of the mouse presenilin-1 gene is introduced by homologous recombination, are examined. The preserved portion of the colony of the ES cells with the desired mutation introduced is taken and used in the process below.

From a pregnant mouse, an embryo at the 8-cell stage is removed. The embryo is sprinkled with about 20 of the above-mentioned preserved ES cells, and then introduced into the uterus of a pseudopregnant female mouse. From among the born young, mice of chimeric coat color are selected. The chimeric mouse is mated with a mouse C57BL/6 strain, and a mouse having the desired mutation can be obtained by the selection of those with agouti coat color from among the born young. The resulting mouse is heterozygote in relation to the presenilin-1 gene introduced with the mutation, whereas the presenilin-1 gene on the other chromosome is a wild type with no mutation.

As starting materials for preparing the probe for the cloning of the chromosomal DNA comprising exon 8 of the mouse presenilin-1 gene from the mouse genomic DNA library, a cDNA of a presenilin-1 gene, which is derived from a mammal other than mouse or human and whose nucleotide sequence has been known, may be used as well as those specifically mentioned in the Examples. As methods for obtaining the DNA fragment used as the probe, a method for a large scale preparation of a plasmid, which comprises a mouse chromosomal DNA comprising a region corresponding to exon 8 of the mouse presenilin-1 gene in chromosomal DNA, or a cDNA of a presenilin-1 gene derived from a mammal other than mouse or human or the like whose nucleotide sequence has been know, can be applied as well as amplification by PCR described in the Examples. Furthermore, after the plasmid is cleaved by restriction enzymes, a desired DNA fragment can be obtained by separating a portion used as the DNA fragment by means of agarose gel electrophoresis and the like.

As a method for labeling the DNA fragment, methods such as those utilizing PCR in the presence of $^{32}$P-dNTP may be used as well as the random priming method described in the Examples. Further, labeling may be introduced by PCR or random priming using a pre-labeled oligodeoxynucleotide as a primer. For the labeling, chemiluminescence using Biotin-Avidin or alkalinephosphatase or the like may also be used, as well as radioisotopes explained in the examples. An RNA fragment labeled by using T3 or T7 RNA polymerase may also be used as a probe. Various methods for preparing a probe are known other than those mentioned above, and a desired probe may be obtained by any method.

For introducing a desired mutation in a DNA, methods specifically described in the Examples can be applied. In addition, a plasmid derived from a bacteriophage such as M13 or a plasmid duplicated using ung *Escherichia coli* is bound complimentarily with an oligodeoxynucleotide synthesized for introducing a mutation at a desired mutation site (bases of the site to be introduced with the mutation are not complimentary), and the resulting complex is used as a primer to prepare a heteroduplex DNA plasmid using a DNA polymerase, and then *Escherichia coli* (ung$^+$) is transformed with the resulting plasmid to obtain a plasmid having a desired mutation. Another method (cassette method) is applied for to obtain a plasmid having a desired mutation, which comprises the steps of synthesizing two oligodeoxynucleotide, which have modified bases to introduce a desired mutation, and are capable of annealing in a mutually complimentary manner and designed to give restriction enzyme sites at both terminals, and ligating the oligodeoxynucleotide to a plasmid for introduction of a mutation using DNA ligase. By appropriately modifying or altering the above methods depending on a purpose, the object may sometimes be more effectively achieved. In addition, as method for introducing a mutation, various methods available in the art are known, and accordingly, any method can be applied to achieve the object.

The targeting vector may preferably comprise a selective marker expression unit as an essential element which comprises a mouse chromosomal DNA fragment introduced with a mutation, a DNA fragment encoding a selective marker, a promoter for controlling transcription thereof, and a terminator. The mouse chromosomal DNA fragment introduced with a mutation is a necessary portion for causing homologous recombination in the ES cell, and the mouse chromosomal DNA fragments flanking the position of the mutation at both sides are also necessary. The target vector thus has a DNA fragment in which only the mutated bases are different from a native mouse chromosomal DNA. The length of the fragment may preferably about 10 kbp, and generally some degree of lengthening or shortening is permissible. However, where the fragment is too short, frequency of homologous recombination may sometimes be lowered.

As selective markers, positive selective markers such as neomycin-resistant gene and hygromycin-resistant gene, and negative selective markers such as thymidine kinase gene of herpes simplex virus and fragment A of diphtheria toxin are known. Any of markers used for cell culture may be used in ES cells. Where a negative selective marker is used, it is necessary to insert the marker outside the mouse chromosomal DNA fragment of the targeting vector. Where a positive selective marker is used, it is necessary to insert the expression unit in an intron in the mouse chromosomal DNA fragment of the targeting vector. When a positive marker is inserted in an exon, the inserted gene generally loses function, and a mouse cannot be sometimes produced which is to be produced for examination of effects of the mutation as an ultimate purpose.

As an ES cell line, cell lines deriving from mouse 129 strain are frequently used. As ES cells deriving from the above mouse strain, ES cells such as D3, CCE, J1, and AB1 may be used as well as R1 described in the Examples. For example, mouse-derived ES cells such as from C57BL/6 mouse strain may also be used other than those from 129 strain. As methods for the introduction of the targeting vector into ES cells, electroporation as described in the Examples may generally applied. Any method may be used so far that the method is usable for the introduction of a plasmid into a cultured cell line, such as Ca phosphate coprecipitation or a liposome method. When ES cells introduced with the targeting vector are cultured in the presence of a selective marker, ES cells that survive and form colonies are possibly received homologous recombination. As a method for determining whether homologous recombination occurs in the ES cells that form the colonies, PCR is typically used. A DNA fragment, an RNA fragment, synthetic oligodeoxynucleotide, antibody or the like that is usable as a probe may be employed.

After ES cells are mixed with a fertilized egg at an early stage of development and then development is continued, a mouse from a sperm or an ova deriving from the ES cell can be obtained. To mix the ES cells in which homologous recombination occurs with the fertilized egg at an early stage of development, a method explained in the Examples may be applied. In addition, a method may also be applied which comprises the steps of removing a fertilized egg at blastula stage from a pregnant mouse, injecting 10 to 20 ES cells to the egg using an injection pipette, transplanting the treated egg into the uterus of a pseudopregnant mouse, and then continuing development to obtain the young.

The fertilized egg at an early stage of development for the use of mixing with the ES cells may be eggs obtained from any strain of mouse. In order to facilitate determination whether or not ES cells is incorporated into the progeny, it is preferable to use a fertilized egg from a mouse strain that has a coat color different from that of a mouse strain from which the ES cells are derived. For example, the ES cells used in the Examples are of agouti-colored 129-strain and the mouse from which the fertilized egg is derived (C57BL/6) has a black colored coat. Using these materials, it is possible to easily select the young which have cells derived from the ES cells by selecting the young with chimera coat color from among the born young. In this case, the young with high proportion of agouti color are most likely to have germ cells derived from the ES cells. The pseudopregnant mouse may be of any strain of mouse.

The mouse used to obtain a mouse with the desired introduced mutation through mating with the resulting chimera mouse may preferably a mouse of a strain with a coat color different from that of a mouse of a strain from which the ES cells are derived. Normally a male chimera mouse is mated with a female of a different strain, and if agouti colored young are obtained, the resulting mice have the desired mutation as heterozygous state. Since a mouse possessing an OS-2 type mutant presenilin-1 gene has a neo expression unit flanked by loxP sequences, it is possible to obtain a mouse in which the neo expression unit is removed can be obtained through mating with a trans-genic mouse with a transferred cre gene.

As explained in the prior art of the present specification, it is believed that a mutation of presenilin-1 protein and presenilin-2 protein promotes the formation of senile plaque due to an increase in Aβ 42 and thereby triggers the onset of Alzheimer's disease. Among trans-genic mice introduced with a gene encoding the mutant APP causing familial Alzheimer's disease, some mice are reported to produce amyloid deposition in the brain (Games D., et al., Nature, Vol. 373, p. 523, 1995, Hsiao K. et al., Science, Vol. 274, p. 99, 1996, Sturchler-Pierrat C. et al., Proc. Natl. Acad. Sci. U.S.A. Vol. 94, No. 24, p. 13287, 1997). In these trans-genic mice, it is considered that amyloid deposition is induced by the increase of the amount of Aβ production in the brain.

By mating a trans-genic animal which is transferred with a gene encoding a mutant APP and capable of forming amyloid deposition in the brain (the animal may be homozygous or heterozygous with reference to the transferred gene) with a PS1 gene-mutated animal of the present invention (the animal may be homozygous or heterozygous with reference to the transferred gene), a hybrid animal can be produced. The animal is preferably as mouse. For mating, either of the above animals may be male.

A portion of the tail of the progeny is collected and chromosomal DNA is extracted. PCR is conducted by using the extracted chromosomal DNA as a substrate and by using as primers two oligodeoxynucleotides each having a nucleotide sequence designed to flank the mutation site of a gene encoding the mutant APP and two oligodeoxynucleotides having a nucleotide sequence designed to flank the mutation site of the mutant PS1 gene.

It is possible to determine whether or not the gene encoding the APP mutant and the mutant PS1 gene of the present invention are incorporated in an extracted chromosomal DNA by carrying out agarose gel electrophoresis of a PCR product, and then observing, for example, presence or absence of bands and mobility of the bands in the gel, and examining the band with the mutation by means of hybridization using an oligodeoxynucleotide having a nucleotide sequence comprising the mutation. PCR may be conducted according to the method described in Example 8. Nucleotide sequences of the oligonucleotides used as the PCR primers may be any sequences so long as they are capable of detecting the gene encoding the APP mutant or the mutant PS1 gene. Based on the results of PCR, an animal having both of the genes each in heterozygous state can be obtained by selection of animals having the gene encoding the APP mutant and the mutant PS1 gene of the present invention.

In order to obtain animals having both of the gene encoding APP mutant and the mutant presenilin-1 gene of the present invention each in homozygous state, an individual animal having both of the genes in homozygous state is selected from the young obtained by mating a suitable male and female selected from the animals having both genes in heterozygous state. To confirm possession of the gene encoding the APP mutant in homozygous state, a potion of the tail of the progeny is taken and chromosomal DNA is extracted, and after the cleavage of the extracted chromosomal DNA with restriction enzyme, electrophoresis is conducted using agarose gel or acrylamide gel. The DNA is then blotted onto a membrane filter, and Southern blotting is performed using as a probe an oligodeoxynucleotide having a sequence which enables binding specifically to a gene encoding the APP mutant, and then density of the resulting bands are measured.

Similarly to the above process, possession of the mutant presenilin-1 gene of this invention in a homozygous state can be verified. Oligodeoxynucleotides used as probes in Southern blotting can be used after being labeled with means ordinarily used in Southern blotting such as a radioactive isotope and a fluorescent dye. A mouse having both of the gene encoding the APP mutation and the mutant presenilin-1 gene of the present invention can thus be produced. A hybrid mouse produced by the above method is characterized by higher productivity of amyloid β protein in the brain and promoted amyloid deposition.

Using the gene-mutated animal, the cells transferred with the mutant presenilin gene, the plasmid comprising the mutant presenilin gene and the like, it is possible to screen substances useful for preventive and/or therapeutic treatment of Alzheimer's disease and to evaluate their utility. Accumulation of amyloid β in a healthy mammal progresses very slowly, whereas the gene-mutated animal of the present invention has a characteristic feature of higher productivity of amyloid β. Therefore, by administering variety of test substances to the gene-mutated animal of the present invention, and comparing the animal with non-administered animals or animals administered with a control substance, it is possible to evaluate substances useful for preventive and/or therapeutic treatment of Alzheimer's disease. A typical example of the evaluation includes a screening of test substances, and conditions, pathological observations, pharmacological tests and the like can be applied as examinations.

Where the cells of the present invention are used, cells are isolated from the animal of the present invention for the use as a primary cell culture, and then the cells can be stabilized and made into a subcultured cell line by immortalizing the cells of primary culture by treatment with a virus or the like, subculturing the cells by isolating a portion of the culture and subjecting to further cultivation in a fresh tissue culture medium. The cells of the present invention encompass the primary cell culture such as nerve cells isolated from the gene-mutated animal, as well as subcultured cells, i.e., so-called cell lines, obtained by subculturing the primary culture. When a nerve cell is used as the cell of the present invention, the cell expresses a large amount of amyloid β protein due to a result of the expression of mutant presenilin-1 protein by the cell. Substance which prevent or delay the nerve cell death related to accumulation of amyloid β can be screened and utility thereof can also be evaluated by adding a test substance to an in vitro culture system of such nerve cells, and comparing, for example, cell survival period or surviving cell number after a certain period of time.

EXAMPLES

The present invention will be more specifically explained by way of examples. However, scope of the present invention is not limited to these examples. In the following examples, presenilin-1 gene is occasionally referred to as PS-1.

Example 1

Cloning of Chromosomal DNA containing Exon 8 of Mouse Presenilin-1 (PS-1) Gene

To construct a probe for isolating a chromosomal DNA containing exon 8 of the mouse PS-1 gene, the following two oligodeoxynucleotides were synthesized:

PR-8-U: 5'-GGAATTTTGGTGTGGTCGGGATGAT-3' (SEQ ID NO: 5) (25-mer)
PR-8-L: 5'-GGTCCATTCGGGGAGGTACTTGA-3' (SEQ ID NO: 6) (23-mer)

PCR was carried out by using these two oligodeoxynucleotides as PCR primers and DNA extracted from 129 SVJ mouse genomic library (Stratagene) to obtain amplified DNA fragment of approximately 130 bp. The fragment was then labeled by random priming method in the presence of $^{32}$P-dCTP and then used as probes for screening of the 129 SVJ mouse genomic library. The resulting positive phage clones were examined and confirmed that they carried the desired chromosomal DNA including exon 8 of the mouse PS-1 gene. The cloned chromosomal DNA was designated as Pα and subjected to restriction mapping (FIG. 1).

Example 2

Construction of Plasmid for Introducing Mutation

DNA was extracted from the cloned phage carrying Pα and cleaved with Sal I, and then subjected to electrophoresis on 1.0% agarose gel to collect Pα. After the cleavage with Pst I and Xba I, the product was subjected to electrophoresis on 1% agarose gel to collect a DNA fragment of approximately 600 bp including a nucleotide sequence encoding isoleucine at position 213 of mouse PS-1. The resulting DNA fragment was designated as X-1. X-1 was ligated using T4 ligase to the plasmid pBluescript II KS+ (Stratagene) which was cleaved beforehand with PstI and Xba I, and then used to transform *Escherichia coli* to obtain plasmid pX-1.

Example 3

Introduction of OS-2 Type Mutation

An OS-2 type mutation and a Sau3A I restriction site were newly introduced into the plasmid pX-1 using the following two oligodeoxynucleotides PRL-104 and PRL-105. Both PRL-104 and PRL-105 were 36-mers and complementary to each other:
PRL-104: 5'-TGTGGTCGGGA TGATC* GCCA C̲ CCACTGGAAAGGCCC-3' (SEQ ID NO: 7)
PRL-105: 5'-GGGCCTTTCCAGTGG G̲ TGGCG* ATCATCCCGACCACA-3' (SEQ ID NO: 8)
(The underlined base is changed from a wild-type base to introduce the OS-2 type mutation, i.e., T for PRL-104 and A for PRL-105 in wild types. Asterisked bases are changed from wild-type bases to introduce the Sau3AI site, i.e., T for PRL-104 and A for PRL-105 in wild types.)

Figure 2:
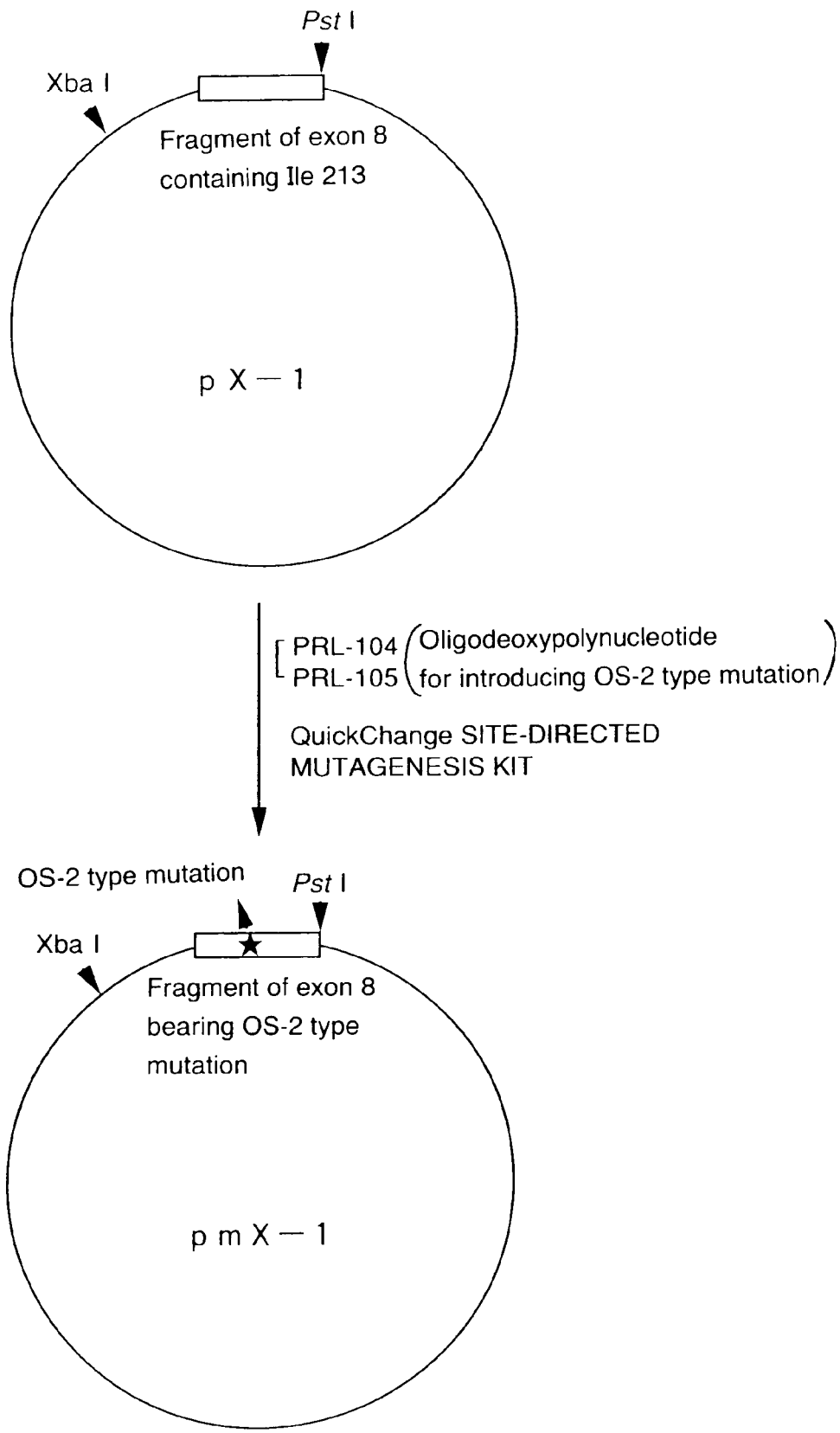
FIG. 2 illustrates a scheme of the construction method of plasmid pmX-1 containing a partial region of exon 8 of the mouse presenilin-1 gene which comprises a region introduced with an OS-2 type mutation by a site-directed mutation technique.

The introduction of the mutation was carried out by using QUICK CHANGE SITE-DIRECTED MUTAGENESIS KIT (Strategene) according to the manufacturer's protocols. Sequencing of the product verified that the mutation was correctly introduced. X-1 bearing the mutation was designated as mX-1, and the plasmid carrying mX-1 was designated as p mX-1 (FIG. 2).

Example 4

Construction of Chromosomal DNA Comprising OS-2 Type Mutation

Figure 3:
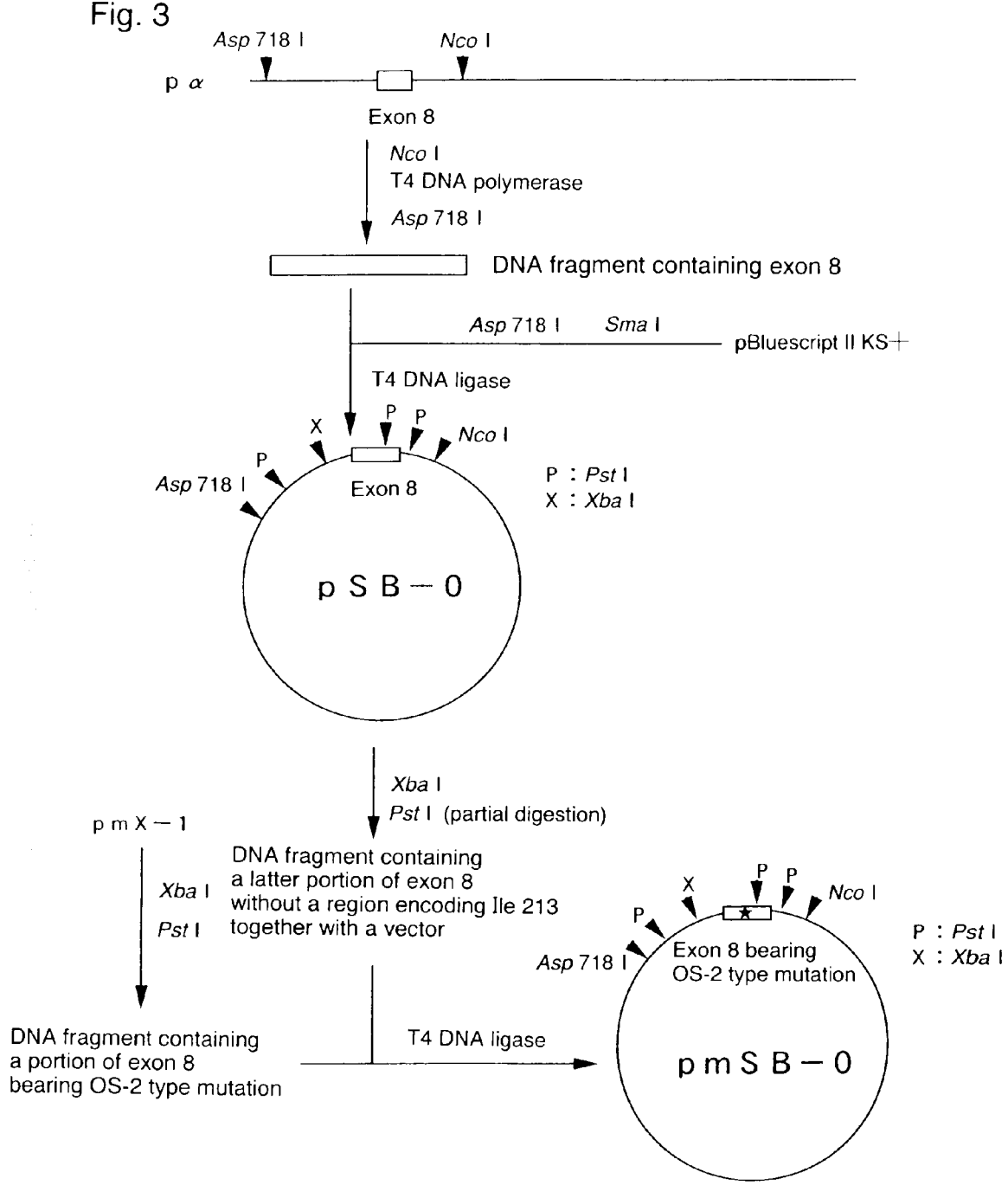
FIG. 3 illustrates a process of preparing a targeting vector.

Pα including exon 8 of the mouse PS-1 obtained in Example 1 was cleaved with Nco I, and then treated with T4 DNA polymerase in the presence of four types of dNTPs to form blunt ends. The resulting fragment was further cleaved with Asp718 I and then subjected to electrophoresis on 1% agarose gel to collect an approximately 5-kbp DNA fragment including exon 8. This fragment was ligated using T4 DNA ligase to the plasmid pBluescript II KS+which was cleaved beforehand with Sam I and Asp718 I, and then transformed into *Escherichia coli* to obtain a plasmid pSB-0. The plasmid pSB-0 was completely cleaved with Xba I, followed by partial digestion with Pst I. Plasmid pmX-1 was cleaved with Xba I and Pst I and subjected to electrophoresis on 1% agarose gel to collect mX-1. The mx-1 was ligated to the Pst I fragment using T4 DNA ligase, and then used to transform *Escherichia coli*. The colonies of transformed *E. coli* were screened to select a colony carrying a plasmid in which the X-1 portion in the plasmid pSB-0 was replaced with mX-1. The plasmid collected was designated as pmSB-0 (FIG. 3).

Figure 4:
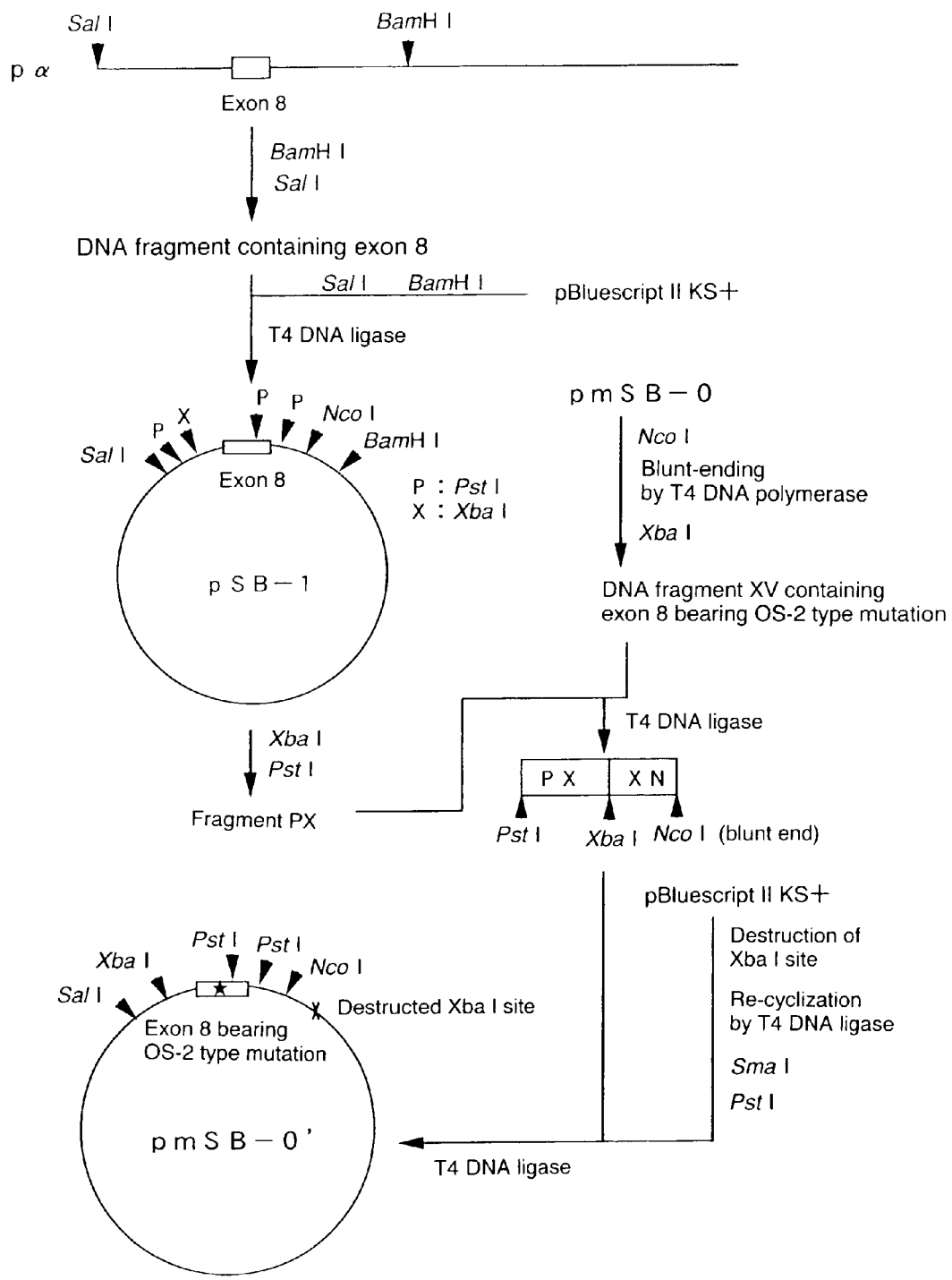
FIG. 4 illustrates a process of preparing a targeting vector.

Separately, Pα was cleaved with BamH I and Sal I and subjected to electrophoresis on 1% agarose gel to collect an approximately 7-kbp DNA fragment including exon 8. This fragment was ligated using T4 ligase to the plasmid pbluescript II KS+ which was cleaved beforehand with BamH I and Sal I, and then used to transform *E. coli* to obtain plasmid pSB-1. The plasmid pmSB-0 was cleaved with Nco I and treated with T4 DNA polymerase in the presence of four types of dNTPs to form blunt ends. The resulting fragment was further cleaved with Xba I and subjected to electrophoresis on 1% agarose gel. An approximately 2.2-kbp DNA fragment XN including exon 8 was collected, and then the fragment and the plasmid pSB-1 were cleaved with Xba I and Pst I, and then the products were subjected to electrophoresis on 1% agarose gel. The collected approximately 2.3-kbp DNA fragment PX not including exon 8 was ligated using T4 DNA ligase. The ligated fragment was further ligated using T4 DNA ligase to the pBluescript II KS+ which was cleaved beforehand with Xba I, blunt-ended with T4 DNA polymerase in the presence of four types of dNTPs, re-ligated using T4 DNA ligase, and cleaved with Sma I and Pst I. The resulting plasmid was subsequently transformed into *E. coli*. The colonies of transformed cells were screened to obtain plasmid pmSB-0' carrying only one DNA fragment in which DNA fragments XN and XP were ligated at the Xba I site (FIG. 4).

Example 5

Construction of Targeting Vector Backbone

To introduce an Eag I site into the Xba I site in plasmid pmSB-0', an oligodeoxynucleotide having the following sequence was synthesized:
5'-CTAGACGGCCGT-3' (SEQ ID NO: 21) (12 mer)
This oligodeoxynucleotide is capable of annealing via a nucleotide sequence having complementarity at the portion of CGGCCG, and forming the following sequence after introduction at a site cleaved with Xba 1.

```
5'-TCTAGACGGCCGTCTAGA-3'      (SEQ ID NO: 22)
3'-AGATCTGCCGGCAGATCT-5'      (SEQ ID NO: 22)
   Xba I  Eag I  Xba I
```

Figure 5:
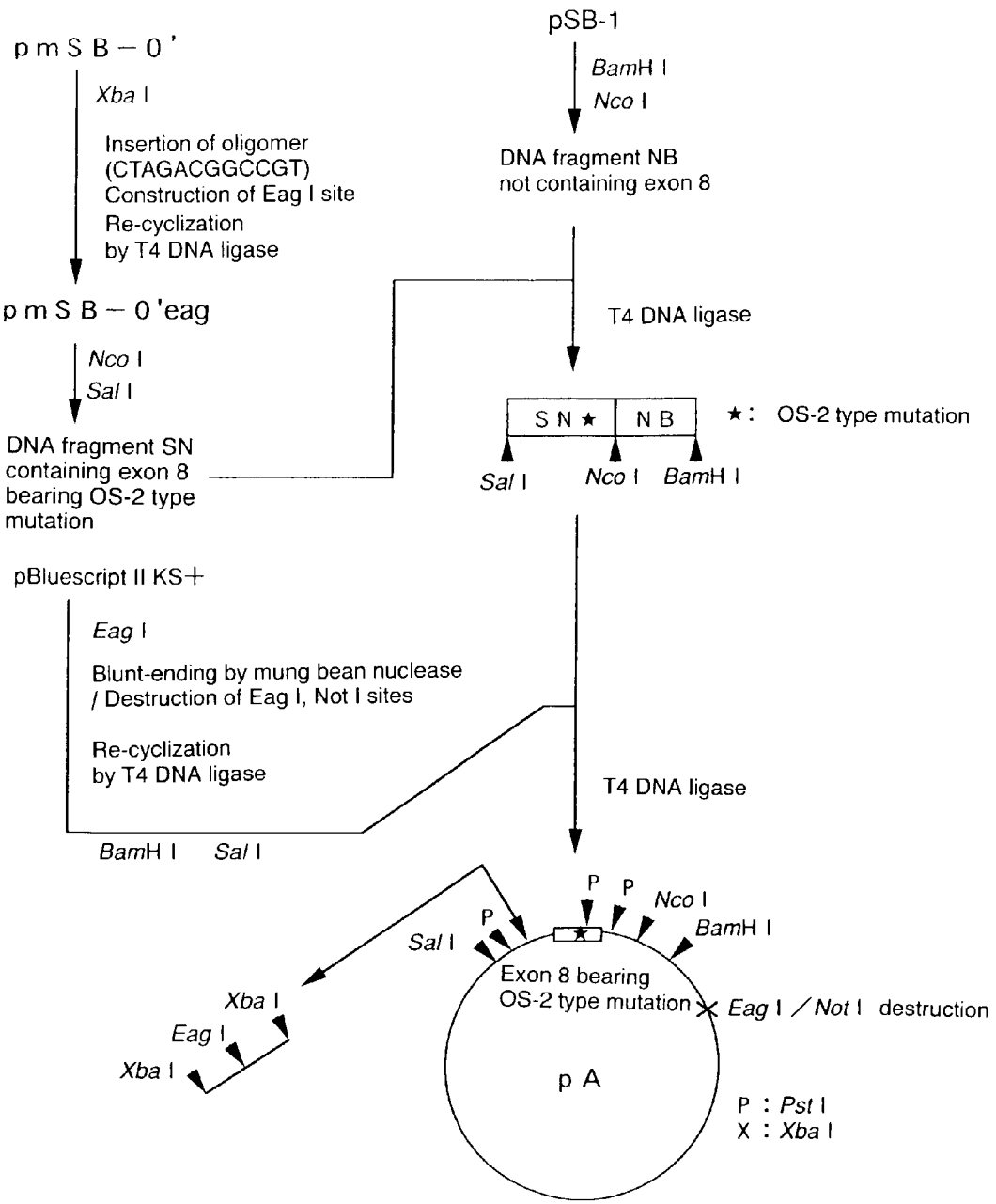
FIG. 5 illustrates a process of preparing a targeting vector.

After the plasmid pmSB-0' was cleaved with Xba I, the above deoxynucleotide was added to the product and ligated using T4 DNA ligase, and then used to transform *E. coli* to obtain a plasmid pmSB-0'eag in which the Eag I site was inserted into the Xba I site of the plasmid pmSB-0'. After cleavage of pmSB-0'eag with Nco I and Sal I, resulting fragments were subjected to electrophoresis on 1% agarose gel to collect an approximately 5.3-kbp DNA fragment SN including exon 8. Separately, plasmid pSB-1 was cleaved with BamH I and Nco I and then subjected to electrophoresis on 1% agarose gel to collect an approximately 2-kbp DNA fragment NB not containing exon 8. The fragments SN and NB were ligated using T4 DNA ligase and treated with BamH I and Sal I to obtain a DNA fragment in which both DNA fragments were ligated at the Nco I site. This DNA fragment was further ligated to pBluescript II KS+using T4 NDA ligase and then used to transform *E. coli* to obtain a plasmid pA (FIG. 5), wherein the pBluescript II KS+was cleaved beforehand with Not I, blunt-ended with mung bean nuclease, re-ligated using T4 DNA ligase to break the Not I site and the Eag I site overlapping with the site, and cleaved with BamH I and Sal I.

Example 6

Construction of Targeting Vector

Figure 6:
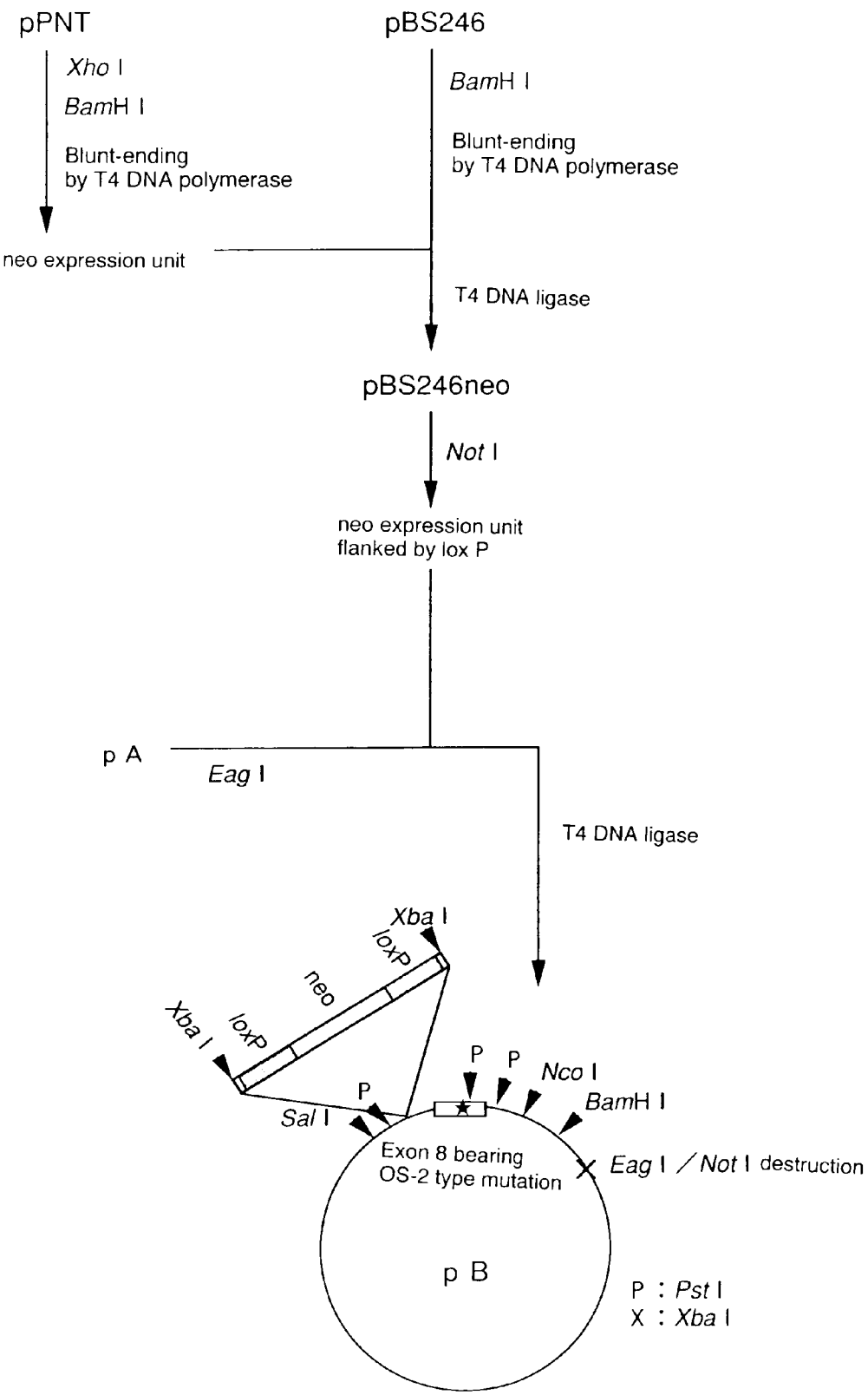
FIG. 6 illustrates a process of preparing a targeting vector.

Plasmid pPNT (Victor L. J. et al., Cell Vol. 65, p. 1153, 1991) was cleaved with Xho I and BamH I and then treated with T4 DNA polymerase to form blunt ends and subjected to electrophoresis on 1% agarose gel. The collected approximately 1.7-kbp DNA fragment containing a neo expression unit was ligated using T4 DNA ligase to the plasmid pBS246 (GIBCO BRL) which was cleaved beforehand with BamH I and treated with T4 DNA polymerase to form blunt ends, and then used to transform E. coli to obtain a plasmid pBS246neo. The plasmid was cleaved with Not I and then subjected to electrophoresis on 1% agarose gel to collect an approximately 2-kbp DNA fragment including the neo expression unit flanked by loxP sequences. The obtained DNA fragment was ligated using T4 DNA ligase to the plasmid pA which was cleaved beforehand with Eag I, and then used to transform E. coli. Colonies of transformed cells were screened to obtain plasmid pB in which the neo gene and the PS-1 gene were oriented in the same direction (FIG. 6).

Figure 7:
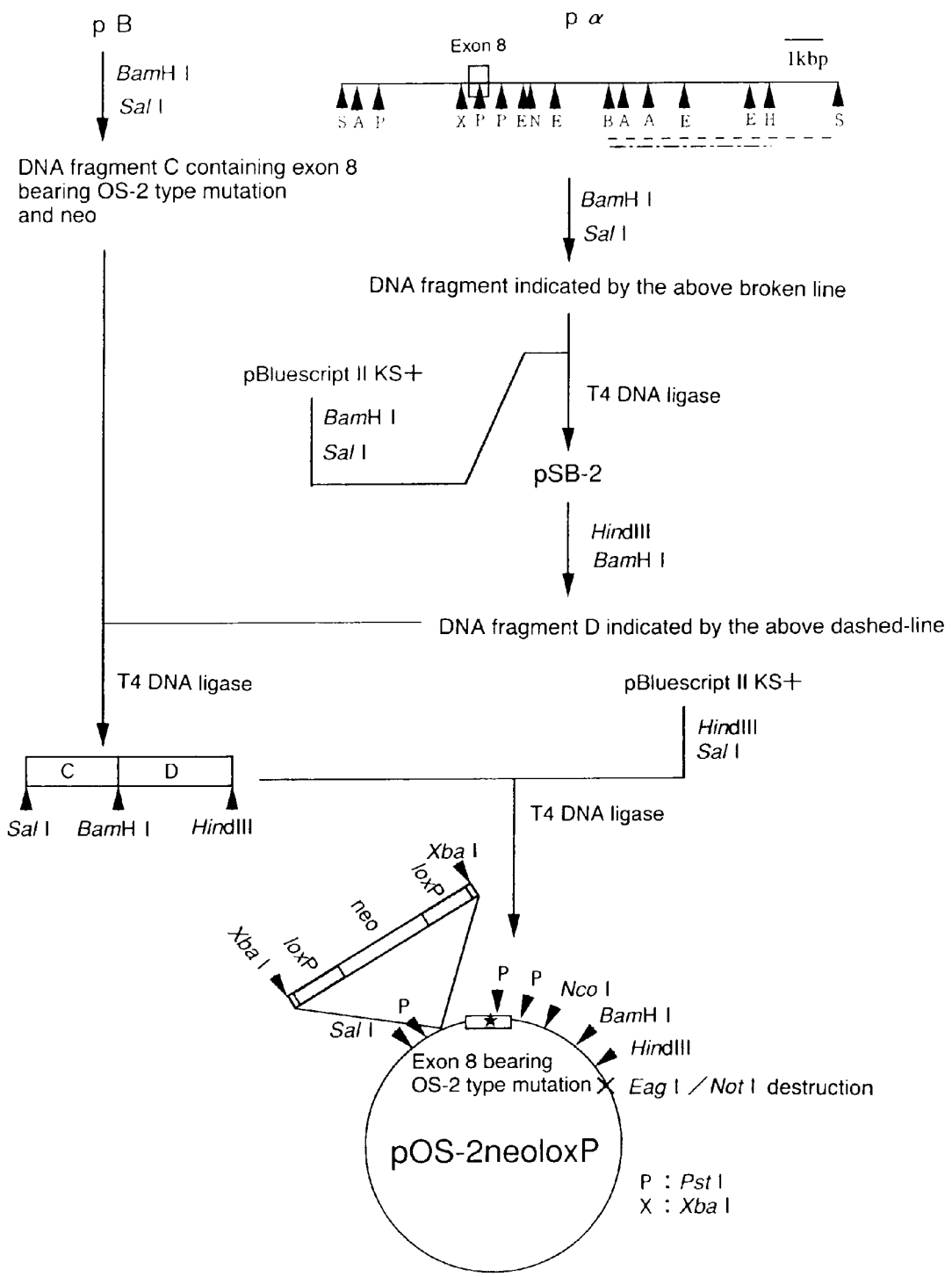
FIG. 7 illustrates a process of preparing a targeting vector and the structure of the targeting vector pOS-2 neoloxP.

After cleavage of the plasmid pB with BamH I and Sal I, the resulting fragments were subjected to electrophoresis on 1% agarose gel to collect a DNA fragment C containing the OS-2 type mutation and the neo expression unit flanked by loxP sequences. Similarly, Pα was cleaved with Sal I and BamH I, and the resulting DNA fragment of approximately 6.5 kbp was subcloned into pbluescript II KS+ to construct a plasmid pSB-2, which was then cleaved with Hind III and BamH I and subjected to electrophoresis on 1% agarose gel to collect a DNA fragment D of approximately 4 kbp. DNA fragments C and D were ligated using T4 DNA ligase, and then the product was cleaved with Hind III and Sal I to obtain a DNA fragment in which C and D were ligated at the BamH I site. The obtained DNA fragment was further ligated using T4 DNA ligase to the pBluescript II KS+which was cleaved beforehand with Hind III and Sal I, and then used to transform E. coli to obtain a targeting vector pOS-2neoloxP (FIG. 7).

Example 7

Introduction of Targeting Vector into ES Cells

Hereinafter in the examples, culture was carried out in an incubator at 37° C. under 5% $CO_2$. The targeting vector was introduced by electroporation into ES cells (R1) which were maintained in DMEM medium supplemented with 15% FBS and $10^3$ units/ml LIF (ESGRO) (the DMEM medium is hereinafter abbreviated as ES medium). Culture medium was replaced with fresh ES medium one day before electroporation, and the R1 cells were collected and washed with electroporation buffer (20 mM HEPES, pH 7.05, 137 mM NaCl, 5 mM KCl, 0.7 mM $Na_2HPO_4$, 6 mM dextrose). R1 cells ($10^7$ cells) were mixed with 25 µg of the targeting vector pOS-2neoloxP, which was linearized using Not I, and 0.8 ml electroporation buffer in an electroporation cuvette. After 1 to 2 minutes, pulses were applied to the cells using Bio-Rad GenePulser (Bio-Rad) under pulse conditions of 240 V and 500 µF. The ES cells were collected by centrifugation and suspended in 30 ml ES medium. The ES cell suspension (2 ml) was put in each 10 ml culture dish in which feeder cells were put in 8 ml ES medium. G418 (titer, 150 µg/ml) was added to the culture after 12 to 18 hours, followed by one-week culture. As the feeder cell, a fibroblast established by the present inventors was used which was isolated from an embryo of 12 to 13 days obtained by mating a HS1 knockout male mouse (I. Taniuchi et al., EMBO J, vol. 14, p. 3664, 1995) with an ICR female mouse of wild-type.

Example 8

Isolation of ES Cells with Homologous Recombination

Colonies of ES cells that were formed in Example 7 by one-week cultivation after the addition of G418 were collected. Each colony was divided into two portions. One portion was subjected to further cultivation. For selection of clones in which homologous recombination occurred, the other portion was washed with PBS, treated with Proteinase K, and then chromosomal DNA was collected and subjected to PCR to select clones. Nucleotide sequences of the synthetic primers used in PCR reaction were as follows.

Prsn1–2: 5'-CCCAACTCTATTTCTACCCTCGT-TCATCTG-3' (SEQ ID NO: 11) (nucleotide sequence outside the targeting vector constructed)

PKG-1: 5'-TAGTGAGACGTGCTACTTCCATTTGT-CACG-3' (SEQ ID NO: 12) (nucleotide sequence in the neo expression unit)

PCR reaction was carried out for 35 cycles under the following conditions: 30 seconds at 93° C., 1 minute at 60° C., and 3 minutes at 68° C. per cycle. The PCR product was analyzed by 1% agarose gel electrophoresis to identify a positive clone which gave a band at an expected position. The clone evaluated as positive was further subjected to PCR using oligodeoxynucleotides PRL-101 and PRL-102. The resulting PCR product was cleaved with Sau3A I and then subjected to electrophoresis on 2% agarose gel. Introduction of the mutation was verified by split bands, and ES cells in which desired homologous recombination occurred were selected. Nucleotide sequences of PRL-101 and PRL-102 were as follows.

PRL-101: 5'-TGCTGGAGGAAAATGTGTTATTTAA-GAGCA-3' (SEQ ID NO: 13)

PRL-102: 5'-TACTGAAATCACAGCCAAGATGAGC-CATGC-3' (SEQ ID NO: 14)

Example 9

Production of Knockin Mouse

ES cells verified to have homologous recombination were further cultured for 4 days and then treated with trypsin to separate one another. An eight-celled embryo was taken from a BDF1 female mouse which was mated with a BDF1 male mouse, and its zona pellucida was then removed. The ES cells separated from one another were attached to the naked embryo (20 ES cells per 8-celled embryo). Th treated embryo was transferred into the uterus of a pseudopregnant female mouse and embryonic development was continued to produce chimeric mice. The resulting chimeric male mouse was mated with a C57BL/6 female mouse. From among their progeny, mice with agouti color were chosen. A portion of the tail was excised, and chromosomal DNA was extracted from each sample. PCR was carried out using PRL-101 and PRL-102, and the PCR product was cleaved with Sau3A I and then subjected to electrophoresis on 2% agarose gel. The presence of cleaved bands was examined to verify that the selected progeny possessed the OS-2 type mutation. One male mouse was chosen from the verified mice and designated as #2.

Example 10

Figure 8:
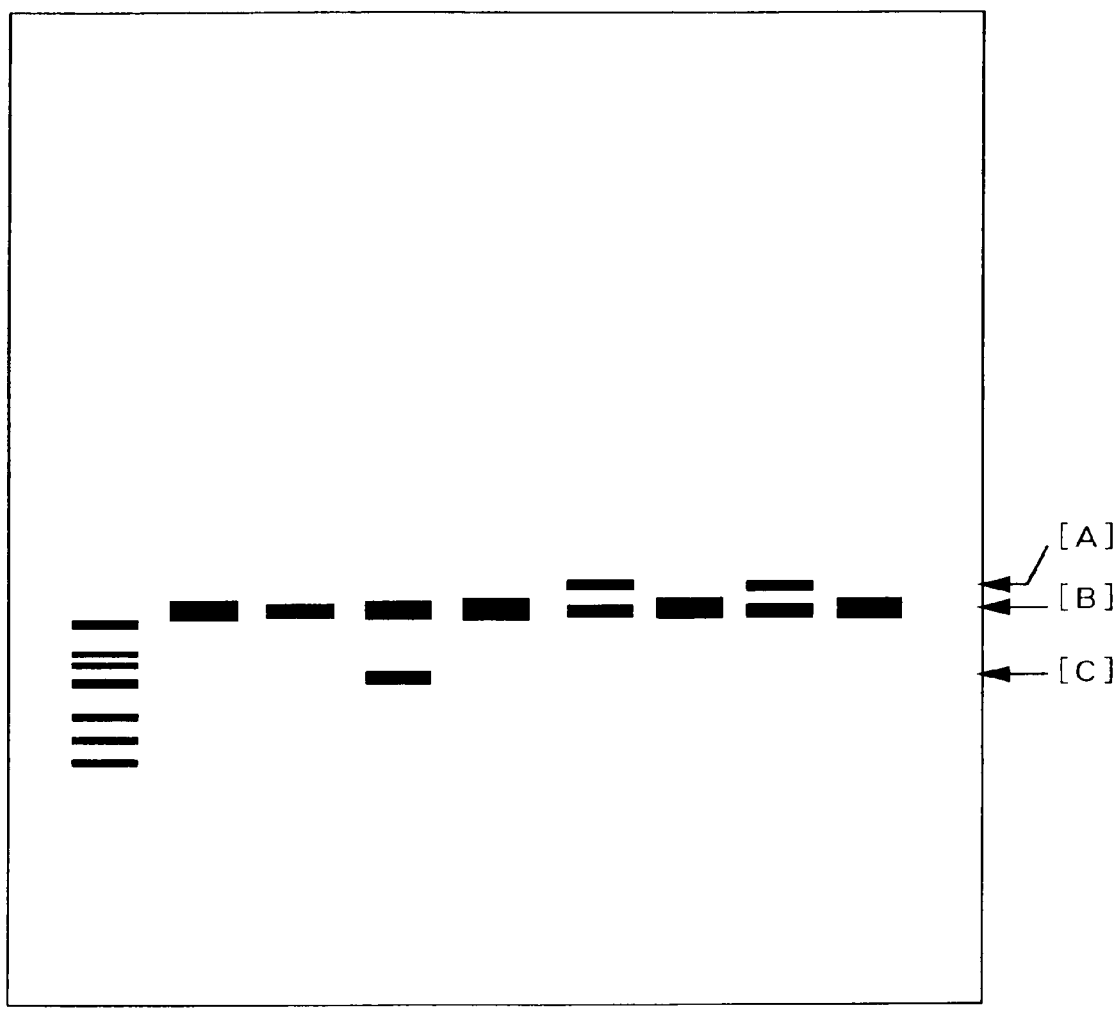
FIG. 8 illustrates results of electrophoresis on 1% agarose gel of the PCR product obtained by mating #2 mouse (male) having OS-2 mutant presenilin-1 gene with F4 of CAG-cre#13 mouse (female), cutting a small piece off from the resulting progeny's tail, obtaining chromosomal DNA from the specimen, and carrying out PCR according to the method described in Example 10. It is shown that mice correspond to 2nd and 4th lanes from the right have no neo expression unit on their chromosomal DNA. In the figure, the leftmost lane shows a molecular weight marker. [A] indicates bands showing neo deficiency on the chromosomal DNA, [B] indicates bands showing that the chromosomal DNA is the wild type, and [C] indicates is bands showing the existence of neo on the chromosomal DNA.

The knockin mouse #2 obtained in Example 9 has the heterozygous neo expression unit flanked by loxPs deriving from the targeting vector. This mouse #2 (male, about 4 months old) was mated with a F4 female of CAG-cre#13 transgenic mouse (2 months old in which transferred cre gene is heterozygous state, K. Sakai et al., Biochem. Biophys. Res. Commun. 217:318, 1997). PCR was carried out using oligodeoxynucleotides PRL-100, PRL-102 and PGK-1 under the conditions described in Example 8. A mouse from which the neo expression unit was removed was chosen as an OS-2 mutated knockin mouse without the neo expression unit (FIG. 8). This mouse was heterozygous with reference to OS-2 type mutation, and had one loxP. Nucleotide sequences of PRL-100, PRL-102, and PGK-1 used for the PCR were as follows.

PRL-100: 5'-GGT CCA TCC CAG CTT CAC ACA GAC MG TCT-3' (SEQ ID NO: 15)

PRL-102: 5'-TAC TGA AAT CAC AGC CM GAT GAG CCA TGC-3' (SEQ ID NO: 16)

PKG-1: 5'-TAG TGA GAC GTG CTA CTT CCA TTT GTC ACG-3' (SEQ ID NO: 17)

INDUSTRIAL APPLICABILITY

The gene-mutated animal of the present invention has a mutated presenilin-1 gene and high productivity of amyloid β due to the gene in comparison with a normal animal without the mutation, and hence the animal exhibits symptoms of Alzheimer's disease through early cell-death or deciduation of neurons in the cerebral hippocampus. Therefore, screening of substances useful for preventive and/or therapeutic treatment of Alzheimer's disease and evaluation of usefulness thereof can be conducted by using the gene-mutated animal of the present invention.

What is claimed is:

1. A knockin gene-mutated mouse having a mutant presenilin-1 gene, wherein the mutant presenilin-1 gene results in overexpression of Amyloid β 42 in the brain of said mouse.

2. The gene-mutated mouse according to claim 1, wherein the animal has a mutant presenilin-1 gene which comprises a DNA having a sequence encoding a presenilin-1 protein in which an amino acid in the amino acid sequence of the presenilin-1 protein is substituted with a different amino acid.

3. The non human gene-mutated mouse according to claim 1, wherein the mouse has the mutant presenilin-1 gene wherein a DNA sequence encoding around an amino acid at position 213 in an amino acid sequence of the presenilin-1 protein is mutated to the following sequence:

5'-TGTGGTCGGGATGATYGCC <u>AVC</u> CACTG-GAAAGGCCC-3' (SEQ ID NO: 18)

wherein V represents a base other than T, Y represents T or C, and the underlined bases encode the amino acid at position 213.

4. The non human gene-mutated mouse according to claim 1, wherein the mouse has the mutant presenilin-1 gene wherein a DNA sequence encoding around an amino acid at position 213 in an amino acid sequence of the presenilin-1 protein is mutated to the following sequence:

5'-TGTGGTCGGGATGATMGCC <u>ACC</u> CACTG-GAAAGGCCC-3' (SEQ ID NO: 19)

wherein Y represents T or C, and the underlined bases encode the amino acid at position 213.

5. The gene-mutated mouse according to claim 1, wherein the mouse has the mutant presenilin-1 gene wherein a DNA sequence encoding around an amino acid at position 213 in an amino acid sequence of the presenilin-1 protein is mutated to the following sequence:

5'-TGTGGTCGGGATGATYGCC <u>NNN</u> CACTG-GAAAGGCCC-3' (SEQ ID NO: 20)

wherein each N independently represents A, G, T, or C and NNN represents a codon as triplet bases which encodes an amino acid other than isoleucine, Y represents T or C, and the underlined bases encode the amino acid at position 213.

6. The non human gene-mutated mouse according to claim 1, wherein the mutant presenilin-1 gene is transferred by homologous recombination.

7. A knockin gene-mutated mouse having a mutant presenilin-1 gene which comprises a DNA having a sequence encoding a mutant mouse presenilin-1 protein in which isoleucine at position 213 of a mouse presenilin-1 protein as set forth in SEQ ID NO: 3 is substituted with an amino acid other than isoleucine, wherein the mutant presenilin-1 gene results in overexpression of Amyloid β 42 in the brain of said mouse.

8. A knockin gene-mutated mouse having a mutant presenilin-1 gene which comprises a DNA having a sequence encoding a mutant mouse presenilin-1 protein in which isoleucine at position 213 of a mouse presenilin-1 protein as set forth in SEQ ID NO: 3 is substituted with threonine, wherein the mutant presenilin-1 gene results in overexpression of Amyloid β 42 in the brain of said mouse.

9. A gene-mutated mouse having a mutant presenilin-1 gene which encodes for the OS-2 type mutation of presenilin-1, wherein the mutant presenilin-1 gene results in overexpression of Amyloid β42 in the brain of said mouse.

10. A method for evaluating the therapeutic effect or preventive treatment of a substance on Alzheimer's disease, which comprises:

administering a test substance to a gene-mutated mouse according to claim 1, then determining a total amount of amyloid β in the brain (M) and the amount of amyloid β 40 and amyloid β 42 in the brain, then calculating a ratio of amyloid β 42/amyloid β 40 (P);

administering a reference substance to a gene-mutated mouse according to claim 1, then determining a total amount of amyloid β in the brain (N) and the amount of amyloid β40 and amyloid β 42 in the brain, then calculating a ratio of amyloid β 42/amyloid β40 (Q); and comparing the value of M to N, or the value of P to Q.

11. The method for evaluation according to claim 10, wherein the comparison is conducted for one or more items selected from the group consisting of survival period of time, exploratory behavior, and migratory behavior.

12. A primary cell culture or a subcultured cell obtainable by isolating a cell from the gene-mutated mouse according to claim 1 and culturing said cell by tissue culture.

13. A method for evaluating a medicament for therapeutic and/or preventive treatment of Alzheimer's disease which comprises the step of culturing the primary cell culture or the subcultured cell according to claim 12 in vitro in the presence of a test compound.

14. An embryo introduced with a plasmid comprising a DNA represented by the nucleotide sequence:
5'-TGTGGTCGGGATGATYGCCACCCACTG-GAAAGGCCC-3' (SEQ ID NO: 19)
wherein Y represents T or C.

15. An embryo obtained by homologous recombination using the plasmid according to claim 1.

16. A method for producing a gene-mutated mouse, wherein the method comprises the step of transferring a mutant presenilin-1 gene by homologous recombination into an embryo of a mouse, wherein the mutant presenilin-1 gene is capable of expressing a mutant presenilin-1 protein and inducing production of amyloid β protein in an amount sufficient to form a progressive neural disease in the hippocampus or a peripheral portion of the cerebral cortex of the brain.

17. The method according to claim 16, wherein the gene mutated presenilin-1 mouse is capable of expressing a mutant presenilin-1 protein in which isoleucine at position 213 of a mouse presenilin-1 protein as set forth in SEQ ID NO: 3 is substituted with an amino acid other than isoleucine.

* * * * *

UNITED STATES PATENT AND TRADEMARK OFFICE
CERTIFICATE OF CORRECTION

PATENT NO.       : 7,022,893 B1
APPLICATION NO. : 09/581528
DATED            : April 4, 2006
INVENTOR(S)      : M. Takeda et al.

It is certified that error appears in the above-identified patent and that said Letters Patent is hereby corrected as shown below:

On the title of the printed patent, item (56), References Cited, "6,395,960" should be --6,395,690--.

At column 35, line 26 (claim 1, line 1) of the printed patent, "having" should be --whose genome comprises--.

At column 35, line 27 (claim 1, line 2) of the printed patent, after "wherein" insert --expression of--.

At column 35, line 28 (claim 1, line 3) of the printed patent, "overexpression" should be --accumulation--.

At column 35, line 31 (claim 2, line 2) of the printed patent, "animal" should be --mouse--.

At column 35, line 32 (claim 2, line 3) of the printed patent, after "DNA" delete "having a".

At column 35, line 36 (claim 3, line 1) of the printed patent, after "The" delete "non human".

At column 35, line 37 (claim 3, line 2) of the printed patent, "has" should be --genome comprises--.

At column 35, line 38 (claim 3, line 3) of the printed patent, after "encoding" delete "around".

At column 35, lines 39-40 (claim 3, lines 4-5) of the printed patent, "in an amino acid sequence of the presenilin-1 protein" should be --of a mouse presenilin-1 protein as set forth in SEQ ID NO: 3--.

At column 35, line 42 (claim 3, line 6) of the printed patent, "5'-TGTGGTCGGGATGATYGCC AVC CACTGGAAAGGCCC-3' (SEQ ID NO: 18)" should be --5'-TGTGGTCG GGATGATYGCC AVC CACTGGAAAGGCCC-3' (SEQ ID NO: 18)--.

At column 35, line 45 (claim 3, line 9) of the printed patent, "the underlined bases" should be --wherein AVC--.

UNITED STATES PATENT AND TRADEMARK OFFICE
CERTIFICATE OF CORRECTION

| | | |
|---|---|---|
| PATENT NO. | : 7,022,893 B1 | Page 2 of 5 |
| APPLICATION NO. | : 09/581528 | |
| DATED | : April 4, 2006 | |
| INVENTOR(S) | : M. Takeda et al. | |

It is certified that error appears in the above-identified patent and that said Letters Patent is hereby corrected as shown below:

At column 35, line 47 (claim 4, line 1) of the printed patent, after "The" delete "non human".

At column 35, line 48 (claim 4, line 2) of the printed patent, "has" should be --genome comprises--.

At column 35, line 49 (claim 4, line 3) of the printed patent, after "encoding" delete "around".

At column 35, lines 50-51 (claim 4, lines 4-5) of the printed patent, "in an amino acid sequence of the presenilin-1 protein" should be --of a mouse presenilin-1 protein as set forth in SEQ ID NO: 3--.

At column 35, line 52 (claim 4, line 6) of the printed patent, "5'-TGTGGTCGGGATGATMGCC ACC CACTGGAAAGGCCC-3' (SEQ ID NO: 19)" should be --5'-TGTGGTCGGGATGATYGCC ACC CACTGGAAAGGCCC-3' (SEQ ID NO: 19)--.

At column 35, line 54 (claim 4, line 8) of the printed patent, "the underlined bases" should be --wherein ACC--.

At column 35, line 57 (claim 5, line 2) of the printed patent, "has" should be --genome comprises--.

At column 35, line 58 (claim 5, line 3) of the printed patent, after "encoding" delete "around".

At column 36, lines 58-59 (claim 5, lines 3-4) of the printed patent, "in an amino acid sequence of the presenilin-1 protein" should be --of a mouse presenilin-1 protein as set forth in SEQ ID NO: 3--.

At column 35, line 62 (claim 5, line 6) of the printed patent, "5'-TGTGGTCGGGATGATYGCC NNN CACTGGAAAGGCCC-3' (SEQ ID NO: 20)" should be --5'-TGTGGTCGGGATGATYGCC NNN CACTGGAAAGGCCC-3' (SEQ ID NO: 20)--.

At column 35, line 67 (claim 5, line 11) of the printed patent, "the underlined bases" should be --wherein NNN--.

UNITED STATES PATENT AND TRADEMARK OFFICE
CERTIFICATE OF CORRECTION

PATENT NO.        : 7,022,893 B1
APPLICATION NO.   : 09/581528
DATED             : April 4, 2006
INVENTOR(S)       : M. Takeda et al.

It is certified that error appears in the above-identified patent and that said Letters Patent is hereby corrected as shown below:

At column 36, line 25 (claim 6, line 1) of the printed patent, after "The" delete "non human".

At column 36, line 26 (claim 6, line 2) of the printed patent, after "transferred" insert --into a mouse ES cell genome--.

At column 36, line 28 (claim 7, line 1) of the printed patent, "having" should be --whose genome comprises--.

At column 36, line 29 (claim 7, line 2) of the printed patent, after "DNA" delete "having a".

At column 36, line 33 (claim 7, line 6) of the printed patent, after "wherein" insert --expression of--.

At column 36, line 34 (claim 7, line 7) of the printed patent, "overexpression" should be --accumulation--.

At column 36, line 37 (claim 8, line 1) of the printed patent, "having" should be --whose genome comprises--.

At column 36, line 38 (claim 8, line 2) of the printed patent, after "DNA" delete "having".

At column 36, line 42 (claim 8, line 6) of the printed patent, after "wherein" add --expression of--.

At column 36, lines 42-43 (claim 8, lines 6-7) of the printed patent, "overexpression" should be --accumulation--.

At column 36, line 45 (claim 9, line 1) of the printed patent, "having" should be --whose genome comprises--.

At column 36, line 46 (claim 9, line 2) of the printed patent, "the" should be --an--.

At column 36, line 47 (claim 9, line 3) of the printed patent, after "wherein" add --expression of--.

UNITED STATES PATENT AND TRADEMARK OFFICE
CERTIFICATE OF CORRECTION

PATENT NO. : 7,022,893 B1
APPLICATION NO. : 09/581528
DATED : April 4, 2006
INVENTOR(S) : M. Takeda et al.

It is certified that error appears in the above-identified patent and that said Letters Patent is hereby corrected as shown below:

At column 36, lines 47-48 (claim 9, lines 3-4) of the printed patent, "overexpression" should be --accumulation--.

At column 36, line 53 (claim 10, line 4) of the printed patent, after "mouse" add --whose genome comprises a mutant presenilin-1 gene--.

At column 36, line 59 (claim 10, line 10) of the printed patent, after "mouse" add --whose genome comprises a mutant presenilin-1 gene--.

At column 37, line 4 (claim 12, line 2) of the printed patent, after "cell" add --comprising a mutant presenilin-1 gene--.

At column 37, line 4 (claim 12, line 2) of the printed patent, after "mouse" add --whose genome comprises a mutant presenilin-1 gene--.

At column 37, line 5 (claim 12, line 3) of the printed patent, after "culture" add --,wherein expression of the mutant presenilin-1 gene results in accumulation of Amyloid â 42 in said culture--.

At column 37, line 8 (claim 13, line 3) of the printed patent, delete "the step of".

At column 37, line 8, (claim 13, line 3) of the printed patent, after "culture" add --comprising a mutant presenilin-1 gene--.

At column 37, line 9 (claim 13, line 4) of the printed patent, after "cell" add --comprising a mutant presenilin-1 gene--.

At column 37, line 10 (claim 13, line 5) of the printed patent, after "subcultured cell" add --; and determining effect of said test compound on Amyloid â 42 formation in the cell culture or the subcultured cell--.

At column 37, line 11 (claim 14, line 1) of the printed patent, after "An" add --isolated mouse--.

At column 37, line 11 (claim 14, line 1) of the printed patent, "introduced with a plasmid comprising" should be --whose genome comprises--.

At column 37, line 12 (claim 14, line 2) of the printed patent, after "DNA" add --sequence--.

UNITED STATES PATENT AND TRADEMARK OFFICE
CERTIFICATE OF CORRECTION

PATENT NO. : 7,022,893 B1
APPLICATION NO. : 09/581528
DATED : April 4, 2006
INVENTOR(S) : M. Takeda et al.

It is certified that error appears in the above-identified patent and that said Letters Patent is hereby corrected as shown below:

At column 37, line 16 (claim 15, line 1) of the printed patent, after "an" add --isolated mouse--.

At column 37, line 16 (claim 15, line 1) of the printed patent, after "embryo" add --of claim 14--.

At column 37, lines 16-17 (claim 15, lines 1-2) of the printed patent, "homologous recombination using the plasmid according to claim 1." should be --insertion of a mouse ES cell comprising a DNA sequence represented by the nucleotide sequence: 5'-TGTGGTCGGGATGATYGCCACCCACTGGAAAGGCCC-3' (SEQ ID NO: 19) wherein Y represents T or C.--.

At column 38, line 1 (claim 16, line 1) of the printed patent, after "gene-mutated" add --presenilin-1--.

At column 38, line 2 (claim 16, line 2) of the printed patent, delete lines 2-9 in its entirety and add --comprising introducing a DNA sequence encoding a presenilin-1 mutation into mouse ES cells, permitting the DNA sequence to undergo homologous recombination with the genome of said ES cell, thereby inserting the presenilin-1 mutation into the endogenous presenilin-1 gene, transferring said ES cell comprising the mutant presenilin-1 into a mouse embryo, transferring the embryo to a female mouse and developing the mouse to term.--.

Signed and Sealed this

Sixteenth Day of October, 2007

JON W. DUDAS
*Director of the United States Patent and Trademark Office*